(12) United States Patent
Gregersen et al.

(10) Patent No.: US 12,740,816 B2
(45) **Date of Patent: *Sep. 22, 2026**

(54) ACTIVE COMPRESSION BONE SCREW

(71) Applicant: University of Utah Research Foundation, Salt Lake City, UT (US)

(72) Inventors: Colin S. Gregersen, Salt Lake City, UT (US); T. Wade Fallin, Hyde Park, UT (US); Charles L. Saltzman, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 147 days.

This patent is subject to a terminal disclaimer.

(21) Appl. No.: 18/686,407

(22) PCT Filed: Aug. 1, 2022

(86) PCT No.: PCT/US2022/038993

§ 371 (c)(1),
(2) Date: Feb. 24, 2024

(87) PCT Pub. No.: WO2023/027869

PCT Pub. Date: Mar. 2, 2023

(65) Prior Publication Data

US 2024/0382242 A1 Nov. 21, 2024

Related U.S. Application Data

(63) Continuation of application No. 17/735,854, filed on May 3, 2022, now Pat. No. 11,523,852, and a (Continued)

(51) Int. Cl.
*A61B 17/86* (2006.01)
*A61B 17/00* (2006.01)

(52) U.S. Cl.
CPC .......... *A61B 17/864* (2013.01); *A61B 17/866* (2013.01); *A61B 2017/00862* (2013.01)

(58) Field of Classification Search
CPC .. A61B 17/864; A61B 17/861; A61B 17/7225
See application file for complete search history.

(56) References Cited

U.S. PATENT DOCUMENTS 2,077,804 A 4/1937 Monroe
2,397,545 A 4/1946 Hardinge
(Continued)

FOREIGN PATENT DOCUMENTS

EP 0015671160002 S 7/2009
WO WO2019113115 A1 6/2019

OTHER PUBLICATIONS

Smith & Nephew, Conquest FN Femoral Neck Fracture System, brochure 2018 (8 pgs).

(Continued)

*Primary Examiner* — Zade Coley
(74) *Attorney, Agent, or Firm* — David Meibos; Maywood IP Law

(57) ABSTRACT

A bone screw may be insertable into a bone, and may have a proximal member, a distal member with bone-engaging threads, wherein the distal member is configured to slidably engage the proximal member such that a variable-length cavity is defined within the proximal member and the distal member, and a tension member residing at least partially within the variable-length cavity. The tension member may have a proximal end coupled to the proximal member and a distal end coupled to the distal member such that, in response to motion of the distal member away from the proximal member, the tension member elongates and urges the distal member to move toward the proximal member. The proximal member and the distal member may be
(Continued)

interconnected to share bending loads at a bending transmission feature.

13 Claims, 18 Drawing Sheets

Related U.S. Application Data continuation of application No. 17/412,689, filed on Aug. 26, 2021, now Pat. No. 11,317,956.

(56) References Cited

U.S. PATENT DOCUMENTS 3,051,169 A 8/1962 Leonard
4,275,717 A 6/1981 Bolesky
4,456,005 A 6/1984 Lichty
4,940,467 A * 7/1990 Tronzo ............... A61B 17/8875 606/65
4,947,502 A 8/1990 Engelhardt
4,959,064 A 9/1990 Engelhardt
5,035,712 A 7/1991 Hoffman
5,061,137 A 10/1991 Gourd
5,102,276 A 4/1992 Gourd
5,122,133 A 6/1992 Evans
5,305,203 A * 4/1994 Raab ...................... A61B 90/50 606/1
5,415,660 A 5/1995 Campbell
5,827,285 A * 10/1998 Bramlet ................. A61B 17/80 606/328
5,876,434 A 3/1999 Flomenblit
6,021,343 A * 2/2000 Foley ..................... A61B 90/36 600/417
6,190,395 B1 * 2/2001 Williams ............... A61B 34/20 606/130
6,296,645 B1 10/2001 Hover
6,468,202 B1 * 10/2002 Irion ...................... A61B 90/10 600/117
6,478,802 B2 * 11/2002 Kienzle, III ........... A61B 34/20 600/417
6,511,481 B2 1/2003 von Hoffmann
6,656,184 B1 12/2003 White
6,685,708 B2 2/2004 Monassevitch et al.
6,725,080 B2 * 4/2004 Melkent ............... A61B 6/5235 606/130
6,736,819 B2 5/2004 Tipirneni
6,887,243 B2 5/2005 Culbert
6,887,245 B2 * 5/2005 Kienzle, III ........... A61B 90/36 606/80
6,908,275 B2 6/2005 Nelson
6,908,465 B2 6/2005 von Hoffmann
7,175,626 B2 2/2007 Neff
7,582,107 B2 9/2009 Trail et al.
7,625,395 B2 * 12/2009 Muckter .............. A61B 17/866 606/300
D611,145 S 3/2010 Khalil
D611,225 S 3/2010 Khalil
D625,818 S 10/2010 Khalil
7,877,890 B2 * 2/2011 Weber .................... A61B 90/36 33/645
7,881,770 B2 * 2/2011 Melkent ................... A61B 5/06 606/130
7,901,412 B2 3/2011 Tipirneni
7,905,908 B2 3/2011 Cragg
7,985,222 B2 7/2011 Gall
8,043,333 B2 10/2011 Frigg
8,048,134 B2 11/2011 Partin
8,066,748 B2 11/2011 Lieberman
8,114,141 B2 2/2012 Appenzeller
8,118,952 B2 2/2012 Gall
D657,873 S 4/2012 Khalil
8,216,243 B2 7/2012 Yevmenenko
8,216,398 B2 7/2012 Bledsoe
8,460,349 B2 6/2013 Frenk
8,491,583 B2 7/2013 Gall
8,540,726 B2 9/2013 Yevmenenko
8,551,106 B2 10/2013 Harrold
8,556,969 B2 10/2013 Johnson
8,597,337 B2 12/2013 Champagne
8,679,167 B2 3/2014 Tipirneni
8,690,931 B2 4/2014 Appenzeller
8,702,768 B2 * 4/2014 Tipirneni ............. A61B 17/742 606/320
8,828,067 B2 * 9/2014 Tipirneni ........... A61B 17/8869 606/320
8,864,804 B2 10/2014 Champagne
8,876,821 B2 11/2014 Kinmon
8,961,500 B2 * 2/2015 Dicorleto ............... A61B 34/20 606/1
9,028,534 B2 5/2015 Tipirneni
9,050,108 B2 * 6/2015 Grinberg ............ A61B 17/1622
9,060,809 B2 6/2015 Tipirneni et al.
9,060,824 B2 6/2015 Chien
9,113,976 B2 8/2015 Yevmenenko
9,138,274 B1 9/2015 Biesinger
9,161,793 B2 10/2015 Huebner
9,161,799 B2 * 10/2015 Benson ................ A61B 17/885
9,168,076 B2 10/2015 Patty
9,204,910 B2 12/2015 Epperly
9,283,006 B2 3/2016 Fonte
9,326,805 B2 5/2016 Biedermann
9,339,316 B2 5/2016 Hulliger
9,345,514 B2 5/2016 Robinson
9,364,275 B2 6/2016 Pacheco
9,414,875 B2 8/2016 Appenzeller
9,482,260 B1 11/2016 Krause
9,498,229 B2 11/2016 Harris, Jr.
9,522,019 B2 12/2016 Biedermann
9,539,372 B2 1/2017 Johnson
9,615,869 B2 4/2017 Brown
9,638,491 B2 * 5/2017 Challis ...................... F16B 5/02
9,724,138 B2 8/2017 Palmer
9,724,149 B2 8/2017 Trieu
9,763,712 B2 9/2017 Appenzeller
9,795,412 B2 10/2017 Sinha
9,827,029 B2 11/2017 Hulliger
9,861,413 B2 1/2018 Palmer
9,861,415 B2 1/2018 Biedermann
9,872,712 B2 1/2018 Trieu
9,980,762 B2 5/2018 Anapliotis
10,012,020 B2 7/2018 Li
10,022,001 B1 7/2018 Hawkins
10,022,018 B2 7/2018 Egger
10,032,019 B2 7/2018 Allison
10,062,016 B2 8/2018 Shirai
10,064,670 B2 9/2018 Mootien
10,082,009 B2 9/2018 Trautman
10,082,013 B2 9/2018 Nguyen et al.
10,085,775 B2 10/2018 Biedermann
10,117,695 B2 11/2018 Biedermann
10,130,358 B2 11/2018 Palmer
10,136,930 B2 11/2018 Krause
10,152,013 B2 12/2018 Kusano et al.
10,166,055 B2 * 1/2019 Eekhoff .............. A61B 17/862
10,166,056 B2 1/2019 Warren
10,192,010 B1 1/2019 Ross
10,192,017 B2 1/2019 Bref
10,194,946 B2 2/2019 Stecco
10,202,015 B2 2/2019 Halbauer
10,202,020 B2 2/2019 Hattori
10,212,010 B2 2/2019 Zhang
10,212,014 B2 2/2019 Qu
10,219,850 B2 3/2019 Fumex
10,222,002 B2 3/2019 Yao
10,222,009 B2 3/2019 Woisetschlaeger
10,242,017 B2 3/2019 Berthiaume
10,252,011 B2 4/2019 Garde
10,271,998 B2 4/2019 Lavon
10,272,005 B2 4/2019 Heidingsfelder-Bongard
10,272,015 B2 4/2019 Bonderer
10,291,991 B2 5/2019 Shan
10,292,735 B2 5/2019 Robinson
10,327,826 B2 6/2019 Horrell

(56) References Cited

U.S. PATENT DOCUMENTS 10,405,903 B1 9/2019 Biesinger
10,478,238 B2 11/2019 Palmer
10,531,905 B2 1/2020 Gault
10,555,766 B2 2/2020 Stecco
10,610,266 B2 4/2020 Biedermann
10,610,276 B2 4/2020 Lutz
10,702,324 B2 7/2020 Marek
10,751,101 B2* 8/2020 Biedermann ...... A61B 17/8685
10,806,497 B2 10/2020 Patty
10,856,924 B2 12/2020 Rippe
10,883,532 B2 1/2021 Krause
10,898,249 B2 1/2021 Palmer
11,012,011 B2 5/2021 Uemura
11,012,016 B2 5/2021 Schweitzer, III
11,012,018 B2 5/2021 Sandoval
11,020,158 B2 6/2021 Epperly
11,042,014 B2 6/2021 Themelis
11,062,018 B2 7/2021 Dymond
11,082,007 B2 8/2021 Khlat
11,082,018 B2 8/2021 Petenyi
11,122,002 B2 9/2021 Dennis
11,192,019 B2 12/2021 Viera
11,202,018 B2 12/2021 Imazu
11,212,013 B2 12/2021 Goergen
11,222,016 B2 1/2022 Li
11,232,006 B2 1/2022 Legtchenko
11,272,018 B2 3/2022 Lyman
11,278,335 B2 3/2022 Rowe
11,282,017 B2 3/2022 White
11,291,488 B1 4/2022 O'Flaherty
11,292,011 B2 4/2022 Hosseinifar
11,452,556 B2 9/2022 Rippe
2002/0198527 A1* 12/2002 Muckter .............. A61B 17/866 606/907
2004/0171930 A1* 9/2004 Grimm .................. A61B 90/39 606/80
2005/0131411 A1 6/2005 Culbert
2005/0154296 A1* 7/2005 Lechner ........... A61B 17/00234 600/429
2005/0240190 A1 10/2005 Gall
2006/0015207 A1 1/2006 Weiser
2006/0264954 A1* 11/2006 Sweeney ............ A61B 17/8685 606/328
2007/0260248 A1* 11/2007 Tipirneni ............. A61B 17/683 606/65
2009/0198287 A1 8/2009 Chiu
2009/0254129 A1 10/2009 Tipirneni
2009/0264937 A1 10/2009 Parrott
2010/0076498 A1 3/2010 Tyber
2010/0211115 A1 8/2010 Tyber
2010/0268285 A1 10/2010 Tipirneni
2010/0312245 A1 12/2010 Tipirneni
2011/0004212 A1 1/2011 Gall
2011/0077693 A1* 3/2011 Yu ...................... A61B 17/8615 606/301
2011/0203406 A1 8/2011 Macintyre
2011/0295319 A1 12/2011 Duplessis
2013/0253593 A1 9/2013 Fierlbeck
2013/0310835 A1 11/2013 Gall
2014/0121714 A1 5/2014 Hernandez
2014/0142639 A1 5/2014 Vennard
2014/0257420 A1 9/2014 Fox
2015/0223843 A1 8/2015 Tipirneni
2015/0250515 A1 9/2015 Terrill
2015/0257797 A1 9/2015 Biedermann
2015/0366591 A1 12/2015 Dujovne
2016/0015440 A1 1/2016 Patty
2016/0038203 A1 2/2016 Huebner
2016/0143649 A1* 5/2016 Weekes ............. A61B 17/1622 606/80
2016/0183992 A1 6/2016 Huang
2016/0249964 A1 9/2016 Songer
2016/0287301 A1 10/2016 Mehl
2017/0296245 A1 10/2017 Gault
2018/0071000 A1 3/2018 Pham
2018/0092677 A1* 4/2018 Peterson ............. A61B 17/863
2018/0206897 A1 7/2018 Palmer
2018/0263669 A1* 9/2018 Peterson ............ A61B 17/8605
2018/0311051 A1* 11/2018 Donaldson ............ A61B 34/20
2018/0317989 A1 11/2018 Sellers
2019/0298427 A1 10/2019 Palmer
2019/0374269 A1 12/2019 Kiefer
2020/0038080 A1 2/2020 Palmer
2020/0261121 A1 8/2020 Biedermann
2020/0305938 A1 10/2020 Krumme
2021/0030455 A1 2/2021 Patty
2022/0142691 A1 5/2022 Smith
2022/0175430 A1 6/2022 Rowe
2022/0218400 A1 7/2022 Krumme
2022/0265332 A1 8/2022 O'Flaherty
2022/0280197 A1 9/2022 Blair

OTHER PUBLICATIONS

Medshape, DynaNail Mini Fusion System, The Compression Standard by which Fusion Systems are measured just got smaller, Brochure 2019 (2 pgs).

Medshape, DynaNail Mini Fusion System, Dynaframe CF Deployment System, 2017 (2 pgs).

Medshape, Enovis, Dynanail Helix, Nail System sales sheet, 2022 (2 pgs).

Medline, United Foot & Ankle: Reflex Nitinol Dynamic Disc: A Novel Concept for Screw Dynamization, 2022 1 pg.

ActivOrtho, NiTE Force Compression Implant 2023 (retrieved from: https://activortho.com/#technology) (6 pgs).

International Search Report and Written Opinion dated Nov. 7, 2022 for International Application No. PCT/US2022/038993.

* cited by examiner

ACTIVE COMPRESSION BONE SCREW

CROSS-REFERENCE TO RELATED APPLICATIONS

This application is a U.S. national stage filing under 35 U.S.C. § 371 of International Application No. PCT/US2022/038993, filed on Aug. 1, 2022, which claims priority of U.S. patent application Ser. No. 17/412,689, filed on Aug. 26, 2021, which issued on May 3, 2022 as U.S. Pat. No. 11,317,956 and U.S. patent application Ser. No. 17/735,854 filed on May 3, 2022, which issued on Dec. 13, 2022 as U.S. Pat. No. 11,523,852. All of the foregoing are incorporated as though set forth herein in their entirety.

TECHNICAL FIELD

The present disclosure relates to bone fixation devices, systems, and methods. More specifically, the present disclosure relates to bone screws that can apply compressive force to surrounding bone.

BACKGROUND

Surgical procedures involving fixation of bone portions with bone screws and fasteners can fail or become loose over time due to bending loads, multi-axial forces, and/or off-axis loading scenarios that may be applied to the bone screws during the healing process. Existing bone screws and fasteners may not provide sufficient fixation and strength to overcome these bending loads, multi-axial forces, and/or off-axis loading scenarios.

Further, it has been observed that healing of fractures, fusion of bone portions, and other forms of osteogenesis are facilitated by pressure applied across the bone interface. Existing bone fixation systems often provide pressure when initially applied, but then this pressure subsides over time due to subsidence, resorption, motion of the bone portions involved, loosening of the fastener, and/or other factors.

Accordingly, bone fixation devices, systems, and methods with improved fixation, strength, and bone loading characteristics would be desirable.

SUMMARY

The various bone fixation devices, systems, and methods of the present disclosure have been developed in response to the present state of the art, and in particular, in response to the problems and needs in the art that have not yet been fully solved by currently available bone fixation devices, systems, and methods. In some embodiments, the bone fixation devices, systems, and methods of the present disclosure may provide improved bone fixation and stabilization between two or more bone portions and/or implants.

According to some embodiments, a bone screw may be insertable into a bone, and may have a proximal member, a distal member with bone-engaging threads, wherein the distal member is configured to slidably engage the proximal member such that a variable-length cavity is defined within the proximal member and the distal member, and a tension member residing at least partially within the variable-length cavity. The tension member may have a proximal end coupled to the proximal member and a distal end coupled to the distal member such that, in response to motion of the distal member away from the proximal member, the tension member elongates and urges the distal member to move toward the proximal member. At least one of the proximal member and the distal member may have a bending transmission feature, displaced either proximally or distally from a torque transmission feature that transmits torque from the proximal member to the distal member while permitting slidable engagement of the distal member relative to the proximal member. The proximal member and the distal member may be interconnected to share bending loads at the bending transmission feature.

The torque transmission feature may have torque transmitting surfaces that are oriented closer to a radial direction than a to a circumferential direction, as to a cross section perpendicular to a longitudinal axis of the bone screw.

A proximal portion of the distal member, proximal to the bone-engaging threads, may have an exterior diameter larger than a minor diameter of the bone-engaging threads.

The proximal member may have a proximal member stop feature. The distal member may have a distal member distal stop feature configured to abut the proximal member stop feature to prevent further elongation of the tension member when the tension member is at a maximum length. The tension member may be at least partially formed of a superelastic material. The maximum length may be selected such that a superelastic strain level of the superelastic material is not exceeded.

The distal end may have a distal member coupling interface that can be inserted through a proximal end of the distal member and then coupled to the distal member from within the variable-length cavity.

The proximal member and the distal member may cooperate to define a weakest cross section, as to bending stress, that is distal to a center of the bone screw.

The weakest cross section may be positioned directly proximal to the bone-engaging threads.

The proximal member may have a proximal interior surface that defines a proximal portion of the variable-length cavity. The distal member may have an extension extending proximally of the torque transmission feature, within the proximal portion. The extension may include the bending transmission feature, which may have an engagement surface that presses against the proximal interior surface in response to bending load applied between the proximal member and the distal member.

The proximal member may have a proximal shank and a head that is wider than the proximal shank. The engagement surface may be closer to the head than to the torque transmission feature.

The extension may have a distal end having the engagement surface, and a relief, distal to the engagement surface, having an outside diameter smaller than the engagement surface. The proximal interior surface may have a protrusion that protrudes toward a longitudinal axis of the bone screw and into the relief. The protrusion may act as a proximal member motion stop feature. The relief may define a shoulder that acts as a distal member motion stop feature configured to abut the proximal member stop feature to prevent further elongation of the tension member when the tension member is at a maximum length.

According to some embodiments, a bone screw may be insertable into a bone, and may have a proximal member, a distal member with bone-engaging threads, wherein the distal member is configured to slidably engage the proximal member such that a variable-length cavity is defined within the proximal member and the distal member, and a tension member residing at least partially within the variable-length cavity. The tension member may have a proximal end coupled to the proximal member and a distal end coupled to the distal member such that, in response to motion of the distal member away from the proximal member, the tension member elongates and urges the distal member to move toward the proximal member. At least one of the proximal member and the distal member may have a torque transmission feature that transmits torque from the proximal member to the distal member while permitting slidable engagement of the distal member relative to the proximal member. The torque transmission feature may have torque transmitting surfaces that are oriented closer to a radial direction than a to a circumferential direction, as to a cross section perpendicular to a longitudinal axis of the bone screw.

The distal member may have a proximal end extending proximally into a proximal portion, formed in the proximal member, of the variable-length cavity.

The proximal portion of the distal member may have an extension extending proximally of the torque transmission feature, within the proximal portion of the variable-length cavity.

The torque transmission feature may have a spline defined by the proximal member and the distal member. The torque transmission feature may have a plurality of proximal member teeth that extend toward the distal member, the proximal member teeth having the torque transmitting surfaces, and a plurality of distal member teeth that extend toward the proximal member such that the distal member teeth interdigitate with the proximal member teeth, the distal member teeth having torque receiving surfaces that receive torque from the torque transmitting surfaces.

The torque receiving surfaces may also be oriented closer to the radial direction than to the circumferential direction.

According to some embodiments, a bone screw may be insertable into a bone, and may have a proximal member, a distal member with bone-engaging threads, wherein the distal member is configured to slidably engage the proximal member such that a variable-length cavity is defined within the proximal member and the distal member, and a tension member residing at least partially within the variable-length cavity. The tension member may have a proximal end coupled to the proximal member and a distal end coupled to the distal member such that, in response to motion of the distal member away from the proximal member, the tension member elongates and urges the distal member to move toward the proximal member. A proximal portion of the distal member, proximal to the bone-engaging threads, may have an exterior diameter larger than a minor diameter of the bone-engaging threads.

The distal member may have a torque transmission feature that receives torque from the proximal member while permitting slidable engagement of the distal member relative to the proximal member. The torque transmission feature may be positioned proximal to and adjacent to the bone-engaging threads.

The proximal member may have a proximal shank and a head that is wider than the proximal shank. The distal member may have a distal shank proximal to the bone-engaging threads. At least one of the proximal shank and the distal shank may have an exterior diameter that is not smaller than a major diameter of the bone-engaging threads.

According to some embodiments, a bone screw may be insertable into a bone, and may have a proximal member, a distal member with bone-engaging threads, wherein the distal member is configured to slidably engage the proximal member such that a variable-length cavity is defined within the proximal member and the distal member, and a tension member residing at least partially within the variable-length cavity. The tension member may have a proximal end coupled to the proximal member and a distal end coupled to the distal member such that, in response to motion of the distal member away from the proximal member, the tension member elongates and urges the distal member to move toward the proximal member. The tension member may be at least partially formed of a superelastic material. The proximal member may have a proximal member stop feature. The distal member may have a distal member stop feature configured to abut the proximal member stop feature to prevent further elongation of the tension member when the tension member is at a maximum length. The maximum length may be selected such that a superelastic strain level of the superelastic material is not exceeded.

The maximum length may further be selected such that a fatigue limit of the superelastic material is not exceeded.

The proximal member stop feature may be positioned proximally of a torque transmission feature that transmits torque from the proximal member to the distal member while permitting slidable engagement of the distal member relative to the proximal member.

The proximal member may have a proximal shank and a head that is wider than the proximal shank. The proximal member stop may be closer to the head than to the torque transmission feature.

The proximal member may have a proximal interior surface that defines a proximal portion of the variable-length cavity. The distal member may have an extension extending proximally within the proximal portion. The extension may have a distal end and a relief, distal to the distal end, having an outside diameter smaller than the distal end. The proximal interior surface may have the proximal member stop feature, which may have a protrusion that protrudes toward a longitudinal axis of the bone screw and into the relief. The relief may define a shoulder that acts as the distal member stop feature and is configured to abut the protrusion when the tension member is at a maximum length.

According to some embodiments, a bone screw may be insertable into a bone, and may have a proximal member, a distal member with bone-engaging threads, wherein the distal member is configured to slidably engage the proximal member such that a variable-length cavity is defined within the proximal member and the distal member, and a tension member residing at least partially within the variable-length cavity. The tension member may have a proximal end coupled to the proximal member and a distal end coupled to the distal member such that, in response to motion of the distal member away from the proximal member, the tension member elongates and urges the distal member to move toward the proximal member. The distal end may have a distal member coupling interface that can be inserted through a proximal end of the distal member and then coupled to the distal member from within the variable-length cavity.

The distal member may have a distal interior surface that defines a distal portion of the variable-length cavity. The distal interior surface may define interior threading. The distal member coupling interface may have exterior threading engageable with the interior threading.

The proximal end of the tension member may have an enlargement. The proximal member may have a proximal shank, a head that is wider than the proximal shank, a proximal interior surface that defines a proximal portion of the variable-length cavity, and a proximal aperture that provides access to the proximal portion of the variable-length cavity through the head. The proximal aperture may be sized to permit passage of the distal end of the tension member therethrough. The proximal aperture may define a shoulder on which the enlargement rests upon coupling of the distal member coupling interface to the distal member.

The proximal member may have a proximal shank, a head that is wider than the proximal shank, a proximal interior surface that defines a proximal portion of the variable-length cavity, and a proximal aperture that provides access to the proximal portion of the variable-length cavity through the head. The distal member may have a distal interior surface that defines a distal portion of the variable-length cavity, and a distal aperture that provides access to the distal portion of the variable-length cavity. The proximal aperture and the distal aperture may be sized to permit passage of a K-wire therethrough. According to one embodiment, a method for securing a first bone portion to a second bone portion may include forming a hole in the first bone portion and the second bone portion and inserting a bone screw into the hole. The bone screw may have a proximal member, a distal member, and a tension member with a proximal end coupled to the proximal member and a distal end coupled to the distal member. The method may include applying torque to the bone screw to move the distal member away from the proximal member such that the tension member elongates and urges the distal member to move toward the proximal member. The torque may be transmitted from the proximal member to the distal member via a torque transmission feature. A bending transmission feature, displaced proximally or distally from the torque transmission feature, may be positioned to share bending loads between the proximal member and the distal member.

The torque transmission feature may have torque transmitting surfaces that are oriented closer to a radial direction than a to a circumferential direction, as to a cross section perpendicular to a longitudinal axis of the bone screw.

The distal member may have bone-engaging threads. A portion of the distal member, proximal to the bone-engaging threads, may have a distal exterior diameter that is at least as large as a proximal exterior diameter of a distal-most end of the proximal member.

The proximal member may have a proximal member stop feature. The distal member may have a distal member distal stop feature. The tension member may be at least partially formed of a superelastic material. Applying the torque may include causing the distal member stop feature to abut the proximal member stop feature to prevent further elongation of the tension member at a maximum length of the tension member. The maximum length may be selected such that a superelastic strain level of the superelastic material is not exceeded.

Inserting the bone screw into the hole may include inserting the proximal member and the distal member into the hole, and, after insertion of the proximal member and the distal member into the hole, inserting the tension member into the hole such that a proximal end of the tension member is coupled to the proximal member and a distal end of the tension member is coupled to the distal member.

The distal member may have bone-engaging threads. Inserting the bone screw into the hole may include engaging the second bone portion with the bone-engaging threads. The proximal member and the distal member may cooperate to define a weakest cross section, as to bending stress, that is positioned directly proximal to the bone-engaging threads.

The distal member may be configured to slidably engage the proximal member such that a variable-length cavity is defined within the proximal member and the distal member. The proximal member may have a proximal interior surface that defines a proximal portion of the variable-length cavity. The distal member may have an extension extending proximally of the torque transmission feature, within the proximal portion. The extension may have the bending transmission feature, which may include an engagement surface. Positioning the bending transmission feature to share the bending loads may include positioning the engagement surface to press against the proximal interior surface in response to bending load applied between the proximal member and the distal member.

The extension may have a distal end having the engagement surface, and a relief, distal to the engagement surface, having an outside diameter smaller than the engagement surface. The proximal interior surface may have a protrusion that protrudes toward a longitudinal axis of the bone screw and into the relief. The protrusion may act as a proximal member motion stop feature. The relief may define a shoulder that acts as a distal member motion stop feature. Applying the torque may cause the distal member stop feature to abut the proximal member stop feature to prevent further elongation of the tension member at a maximum length of the tension member.

According to one embodiment, a method for securing a first bone portion to a second bone portion may include forming a hole in the first bone portion and the second bone portion and inserting a bone screw into the hole. The bone screw may have a proximal member, a distal member, and a tension member with a proximal end coupled to the proximal member and a distal end coupled to the distal member. The method may further include applying torque to the bone screw to cause the distal member to move away from the proximal member such that the tension member elongates and urges the distal member to move toward the proximal member. Applying the torque to the bone screw may include transmitting the torque from the proximal member to the distal member via a torque transmission feature with torque transmitting surfaces that are oriented closer to a radial direction than a to a circumferential direction, as to a cross section perpendicular to a longitudinal axis of the bone screw.

The distal member may have an extension, proximal to the torque transmission feature, that extends proximally into the proximal member.

The torque transmission feature may include a plurality of proximal member teeth of the proximal member that extend toward the distal member. The proximal member teeth may have the torque transmitting surfaces. The torque transmission feature may also include a plurality of distal member teeth of the distal member that extend toward the proximal member such that the distal member teeth interdigitate with the proximal member teeth. The distal member teeth may have torque receiving surfaces. Transmitting the torque from the proximal member to the distal member may include receiving the torque from the torque transmitting surfaces at the torque receiving surfaces.

The torque receiving surfaces may also be oriented closer to the radial direction than to the circumferential direction.

According to one embodiment, a method for securing a first bone portion to a second bone portion may include forming a hole in the first bone portion and the second bone portion and inserting a bone screw to insert the bone screw into the hole. The bone screw may have a proximal member with a proximal member stop feature, a distal member with a distal member stop feature, and a tension member formed at least partially of a superelastic material. The tension member may have a proximal end coupled to the proximal member, and a distal end coupled to the distal member. The method may further include applying torque to the bone screw to cause the distal member to move away from the proximal member, such that the tension member elongates and urges the distal member to move toward the proximal member, until the distal member stop feature abuts the proximal member stop feature to prevent further elongation of the tension member at a maximum length of the tension member. The maximum length may be selected such that a superelastic strain level of the superelastic material is not exceeded.

The maximum length may further be selected such that a strength limit of the superelastic material is not exceeded.

Applying the torque may include transmitting the torque from the proximal member to the distal member via a torque transmission feature distal to the proximal member stop feature.

The proximal member may have a proximal shank and a head that is wider than the proximal shank. The proximal member stop may be closer to the head than to the torque transmission feature.

The proximal member and the distal member may cooperate to define a variable-length cavity. The proximal member may have a proximal interior surface within a proximal portion of the variable-length cavity. The distal member may have an extension that extends proximally into the proximal portion of the variable-length cavity. The extension may have a relief. The proximal interior surface may have a protrusion that protrudes toward a longitudinal axis of the bone screw and into the relief. The protrusion may act as a proximal member motion stop feature. The relief may define a shoulder that acts as a distal member motion stop feature. Applying the torque may include causing the distal member stop feature to abut the proximal member stop feature to prevent further elongation of the tension member at a maximum length of the tension member.

According to one embodiment, a method for securing a first bone portion to a second bone portion may include forming a hole in the first bone portion and the second bone portion and inserting a proximal member and a distal member of a bone screw into the hole. The method may further include, after insertion of the proximal member and the distal member into the hole, inserting a tension member of the bone screw into the hole such that a proximal end of the tension member is coupled to the proximal member and a distal end of the tension member is coupled to the distal member. The method may further include, after insertion of the tension member into the hole, applying torque to the bone screw to cause the distal member to move away from the proximal member such that the tension member elongates and urges the distal member to move toward the proximal member.

The proximal member and the distal member may cooperate to define a variable-length cavity. Inserting the tension member into the hole may include inserting the tension member into the variable-length cavity.

The distal member may have a distal interior surface that defines interior threading. The distal member coupling interface may include exterior threading. Inserting the tension member into the variable-length cavity may include engaging the interior threading with the exterior threading.

The proximal end of the tension member may have an enlargement. The proximal member may have a proximal shank, a head that is wider than the proximal shank, a proximal interior surface that defines a proximal portion of the variable-length cavity, and a proximal aperture that provides access to the proximal portion of the variable-length cavity through the head. The proximal aperture may define a shoulder. Inserting the tension member into the variable-length cavity may further include inserting the distal end of the tension member through the proximal aperture and positioning the enlargement to rest on the shoulder of the proximal aperture.

The proximal member may have a proximal aperture that provides proximal access to the variable-length cavity. The distal member may have a distal aperture that provides distal access to the variable-length cavity. The method may further include, prior to insertion of the bone screw into the hole, inserting a K-wire into the hole such that the K-wire is anchored to the second bone portion. Inserting the proximal member and the distal member into the hole may include causing a proximal end of the K-wire to pass through the distal aperture and the proximal aperture.

According to one embodiment, a method for securing a first bone portion to a second bone portion may include forming a hole in the first bone portion and the second bone portion and inserting a bone screw into the hole. The bone screw may include a proximal member comprising a proximal member stop feature, a distal member comprising a distal member stop feature, and a tension member, formed at least partially of a superelastic material. The tension member may have a proximal end coupled to the proximal member and a distal end coupled to the distal member. The method may further include inserting the bone screw to a first insertion depth that creates a first compression load, and inserting the bone screw to a second insertion depth that creates a second compression load that is similar to the first compression load. The second insertion depth may be greater than the first insertion depth. The method may further include inserting the bone screw to a third insertion depth that creates a third compression load that is greater than the second compression load. The third insertion depth may be greater than the second insertion depth.

The difference between the first insertion depth and the second insertion depth may be between 1 mm and 4 mm.

According to one embodiment, a method for accommodating shortening between a first bone portion and a second bone portion fixed together by a bone screw may include forming a hole in the first bone portion and the second bone portion and inserting the bone screw into the hole such that a first compression load is created. The bone screw may include a proximal member comprising a proximal member stop feature, a distal member comprising a distal member stop feature, and a tension member, formed at least partially of a superelastic material. The tension member may have a proximal end coupled to the proximal member and a distal end coupled to the distal member. The bone screw may produce a second compression load that is less than the first compression load upon a first total shortening between first and second bone portions. The bone screw may produce a third compression load that is similar to the second compression load upon a second total shortening between first and second bone portions that is greater than the first total shortening. The bone screw may produce a fourth compression load that is less than the third compression load upon a third total shortening between first and second bone portions that is greater than the second total shortening.

The difference between the second total shortening and third total shortening may be between 1 mm and 4 mm.

These and other features and advantages of the present disclosure will become more fully apparent from the following description and appended claims or may be learned by the practice of the devices, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which.

Figures 1A, 1B, 1C, 1D:
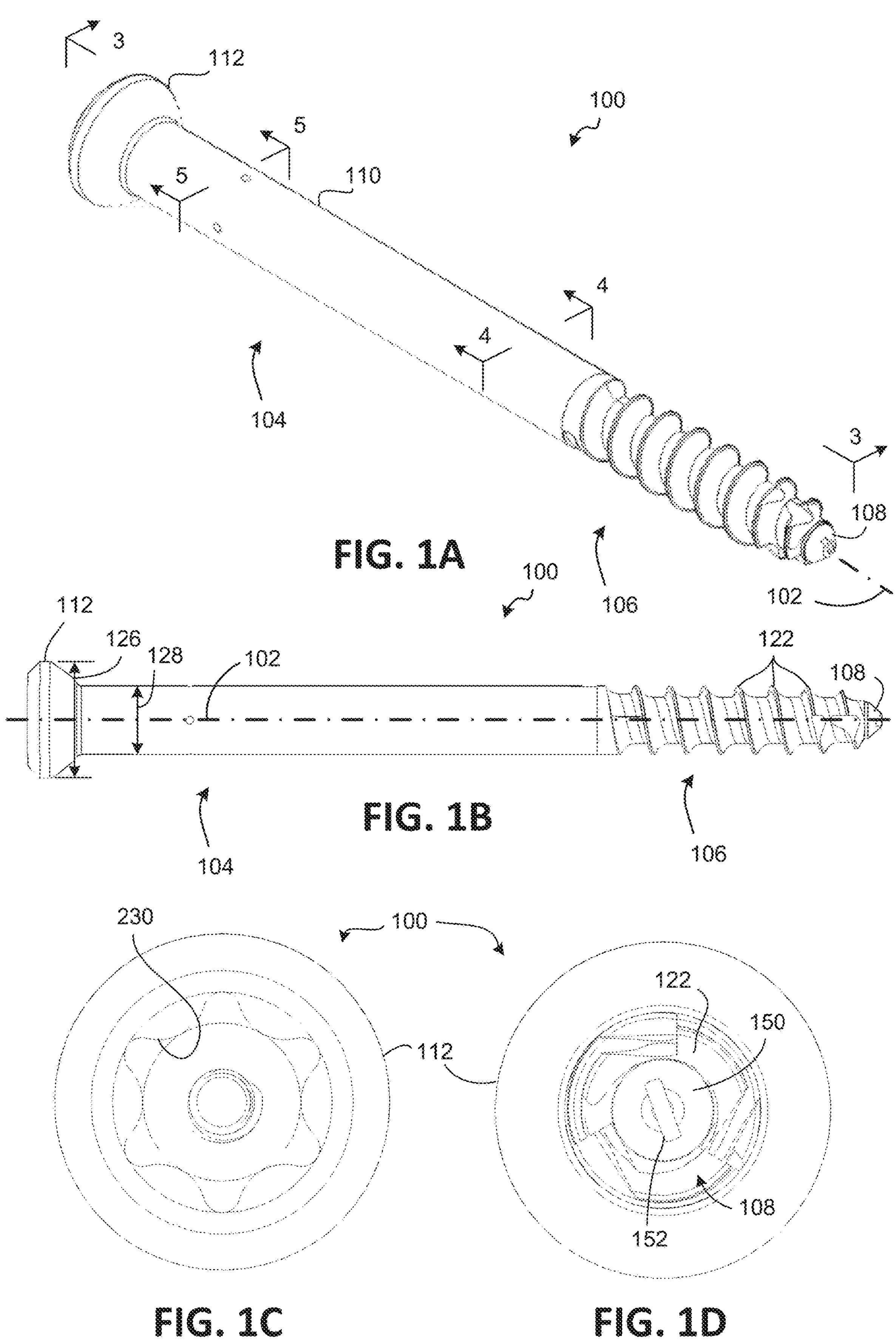
FIGS. 1A, 1B, 1C, and 1D are perspective, side elevation, front elevation, and rear elevation views, respectively, of a bone screw according to one embodiment.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure, but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The following examples have been included to provide guidance to one of ordinary skill in the art for practicing representative embodiments of the presently disclosed subject matter. In light of the present disclosure and the general level of skill in the art, those of skill in the art can appreciate that the following examples are intended to be exemplary only and that numerous changes, modifications, and alterations can be employed without departing from the scope of the presently disclosed subject matter.

Fixation of bone portions with bone screws may be utilized in a variety of surgical procedures including, but not limited to: trauma fixation, arthrodesis, osteotomies, etc. For example, trauma fixation procedures may be needed when high-energy events cause bones to break and fragment. Bone screws may be utilized to secure the bone fragments in a correct anatomic alignment while the bone heals. Arthrodesis procedures can treat degenerative bone joints, which may cause pain and loss of joint function, by removing degraded articular cartilage from a bone joint and then holding the bone joint in compression with bone screws while the bones fuse together across the joint. Osteotomy procedures can realign a bone to a more favorable position, by first cutting the bone and then using bone screws to hold the cut bone portions in a new desired alignment while the bone heals.

Example applications/procedures that may utilize any of the fixation devices described or contemplated herein, in any configuration and with any of the features described herein, may include, but are not limited to: trauma procedures (e.g., fracture fixation, etc.), post-traumatic reconstruction (pelvic or joint fusions), spine procedures (e.g., SI fusion, facet fixation, etc.), joint reconstruction procedures (total hip arthroplasty, total knee arthroplasty), sports related procedures, extremity procedures, cranio-maxillo-facial procedures, rib plating procedures, veterinary procedures, bone plating procedures (e.g., femur plates, humerus plates, tibial plates, etc.), intramedullary nail fixation procedures, amputee connection procedures, sarcoma procedures, shoulder/glenoid fixation, small bone fixation, correction, or fusion (e.g., foot/ankle, hand/wrist, etc.), joint fusions, osteotomies, procedures involving osteoporotic or compromised bone, etc.

The following disclosure presents various bone fixation devices, systems, and methods for utilization in bone and other tissues as implantable devices (e.g., orthopedic implants, spine implants, sports medicine implants, trauma implants, reconstruction implants, extremity implants, veterinary implants, etc.). It will be understood that any feature of any bone fixation assembly described or contemplated herein may be combined with any other bone fixation assembly that is described or contemplated herein without departing from the spirit or scope of the present disclosure.

Figure 2:
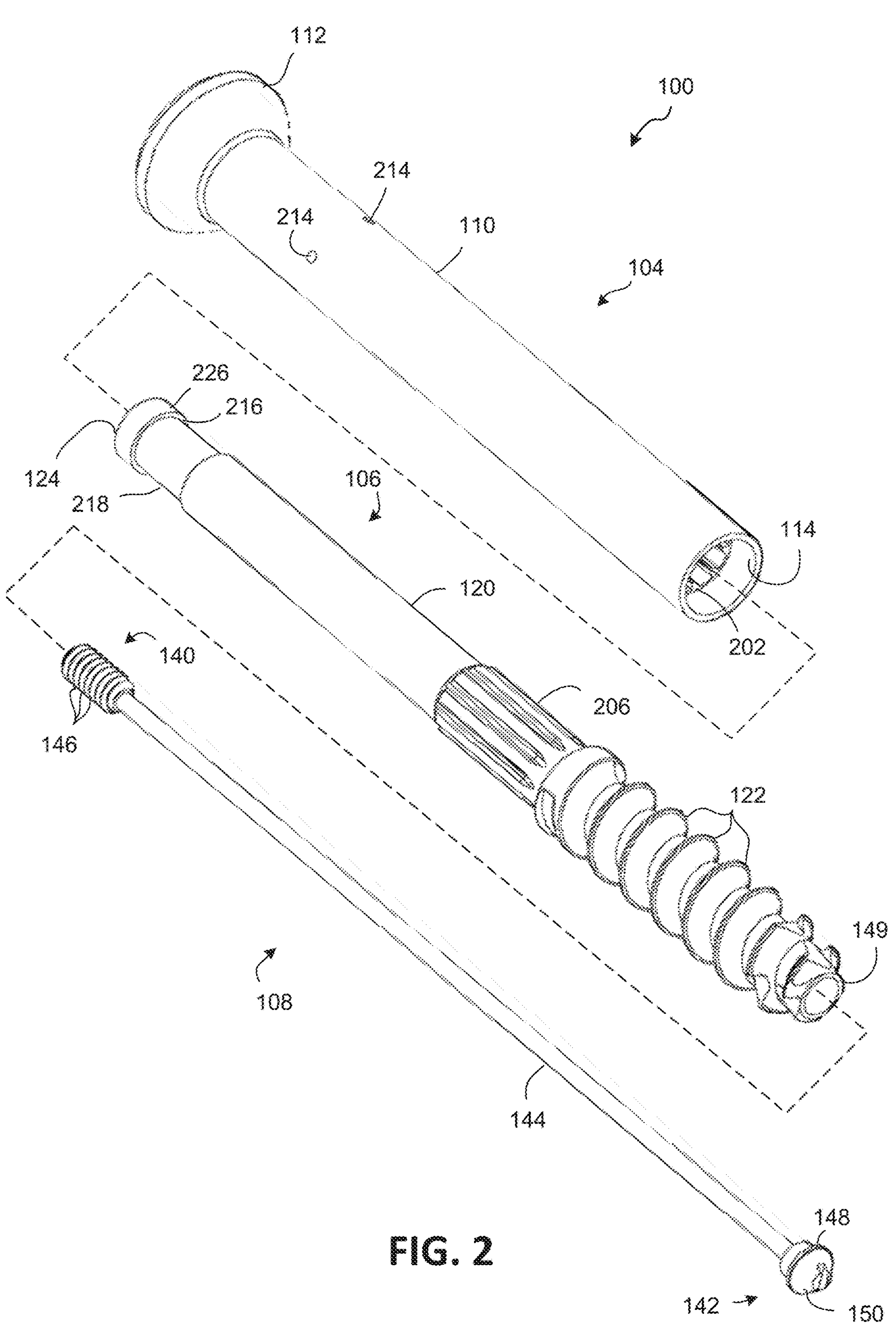
FIG. 2 is an exploded, perspective view of the bone screw of FIG. 1.
Figure 4:
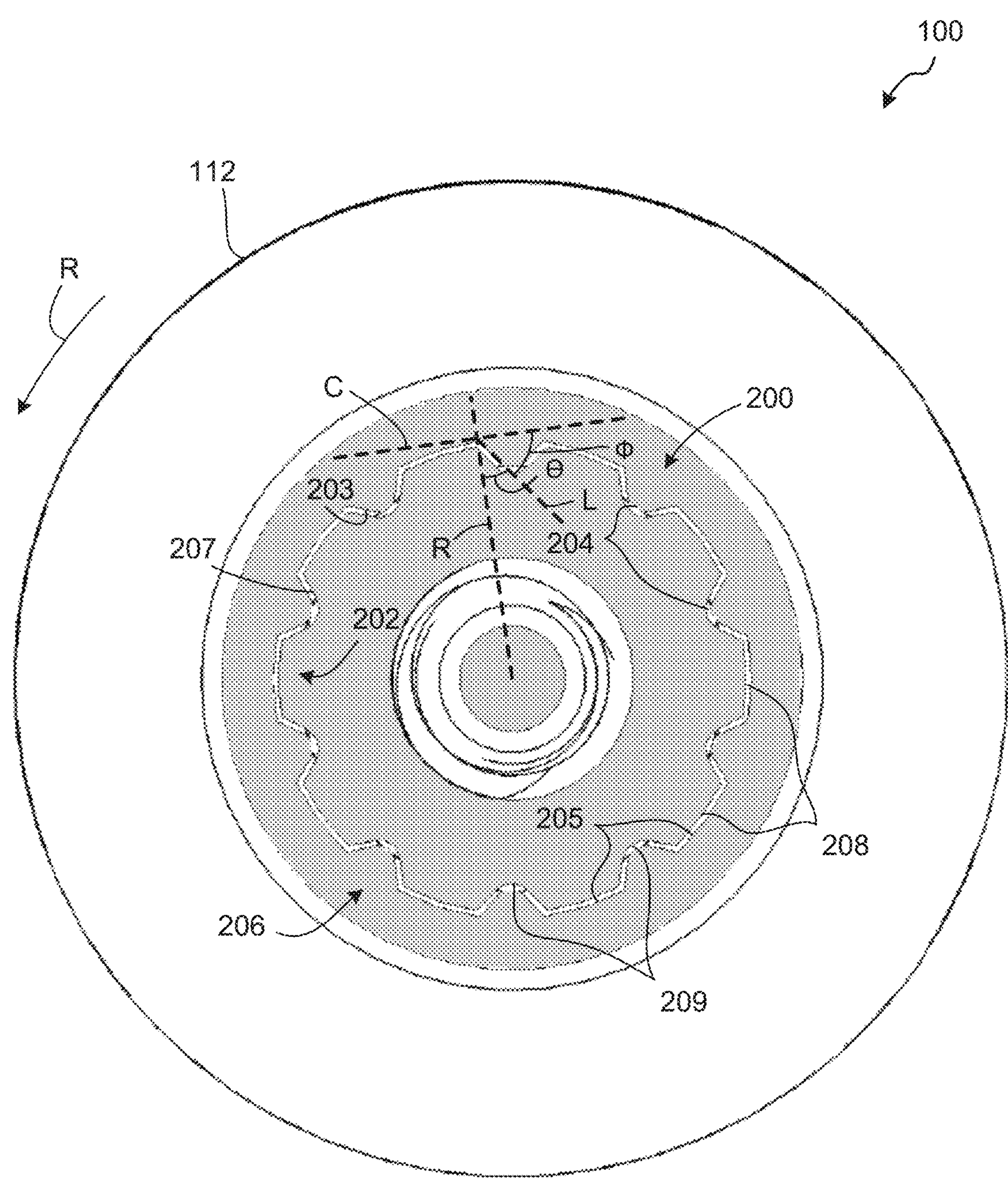
FIG. 4 is a front elevation, section view of the bone screw of FIG. 1.
Figure 5:
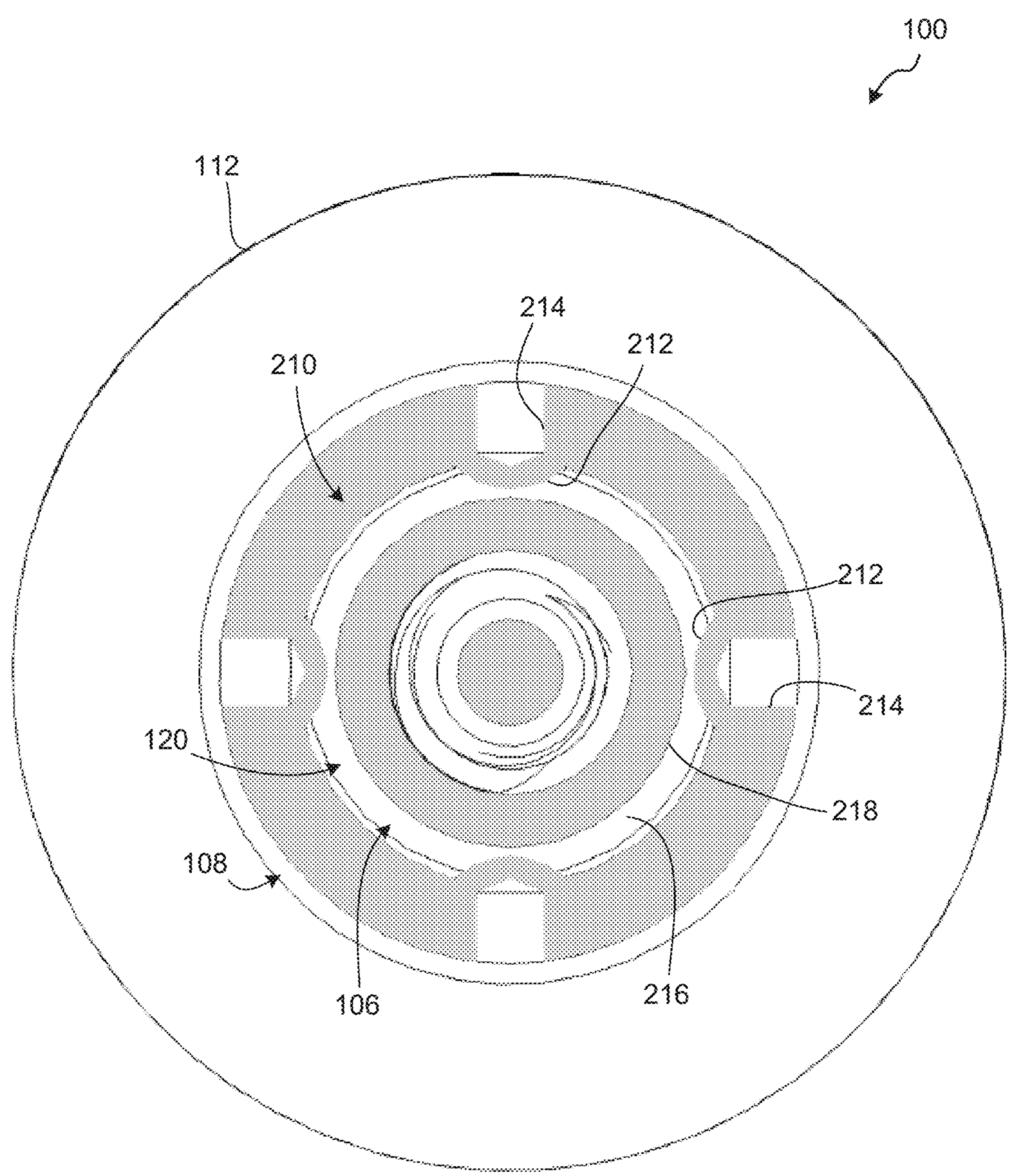
FIG. 5 is another front elevation, section view of the bone screw of FIG. 1.

According to some embodiments, a bone screw 100 may be provided. The bone screw may have a longitudinal axis 102, a proximal member 104, a distal member 106, and a tension member 108. The bone screw 100 will be shown and described in connection with FIGS. 1A through 5. FIGS. 1A, 1B, 1C, and 1D are perspective, side elevation, front elevation, and rear elevation views, respectively, of the bone screw 100. FIG. 2 is an exploded, perspective view of the bone screw 100. FIGS. 3A, 3B, 3C, and 3D are side elevation, section views of the bone screw 100, the proximal member 104, the distal member 106, and the tension member 108, respectively. FIG. 4 is a front elevation, section view of the bone screw 100. FIG. 5 is another front elevation, section view of the bone screw 100.

As shown, the longitudinal axis 102 of the bone screw 100 may be an axis extending along the geometric center and/or axis of radial symmetry of the bone screw 100, along the longest length of the bone screw 100. The terms "proximal" and "distal" are generally used with reference to displacement along the longitudinal axis 102, although they are sometimes used as adjectives to connect features to a proximal or distal member, such as the proximal member 104 and the distal member 106.

The proximal member 104 may have a proximal shank 110 at a distal end of the proximal member 104, a head 112 at a proximal end of the proximal member 104, and a proximal interior surface 114 that cooperates with an interior surface 115 of the proximal member 104 to define a proximal portion 132 of a variable-length cavity 130. The head 112 may have a width 126 (i.e., greatest dimension perpendicular to the longitudinal axis 102) greater than a width 128 of the proximal shank 110. Thus, upon insertion into the bone, the head 112 may protrude transverse to the longitudinal axis 102 to engage the cortex of the bone into which the bone screw 100 is driven, as will be shown subsequently. The proximal interior surface 114 and the interior surface 115 may face inwardly, toward the longitudinal axis 102. The head 112 may have a driver engagement feature 230 that receives torque from a driver (not shown). For example, the driver engagement feature 230 may be a socket with a radially symmetrical pattern that receives a boss, with a matching shape, on the distal end of the driver. The driver engagement feature 230 may be a hexagonal socket as shown.

The distal member 106 may have a distal shank 120 at a proximal end of the distal member 106, bone-engaging threads 122 at a distal end of the distal member 106, and a distal interior surface 124 defining a distal portion 134 of the variable-length cavity 130. The bone-engaging threads 122 may be designed to engage bone, and may be shaped to function optimally upon insertion into a pilot hole previously formed in the bone. In the alternative, the bone-engaging threads 122 may be self-tapping, and may enable the bone screw 100 to form its own pilot hole in the bone into which it is inserted.

The tension member 108 may have a proximal end 140, a distal end 142, and a shank 144, extending along the longitudinal axis 102, that connects the proximal end 140 to the distal end 142. The proximal end 140 may have proximal threads 146 that facilitate coupling of the tension member 108 to the proximal member 104 via threaded engagement with interior threads 147 within the proximal member 104. The distal end 142 may have a distal flange 148 that facilitates coupling of the tension member 108 to the distal member 106 via abutment of the distal flange 148 on a corresponding surface 149 of the distal member 106, distal to the bone-engaging threads 122. The distal end 142 may further have a distal tip 150 that is sufficiently sharp for bone penetration. The distal tip 150 may have one or more features, such as channels or grooves, that help remove bone cuttings from in front of the distal tip 150. Additionally or alternatively, the distal tip 150 may have a slot 152 that facilitates rotation of the tension member 108 with a driver such as a flat-head screwdriver.

Figures 3A, 3B, 3C, 3D:
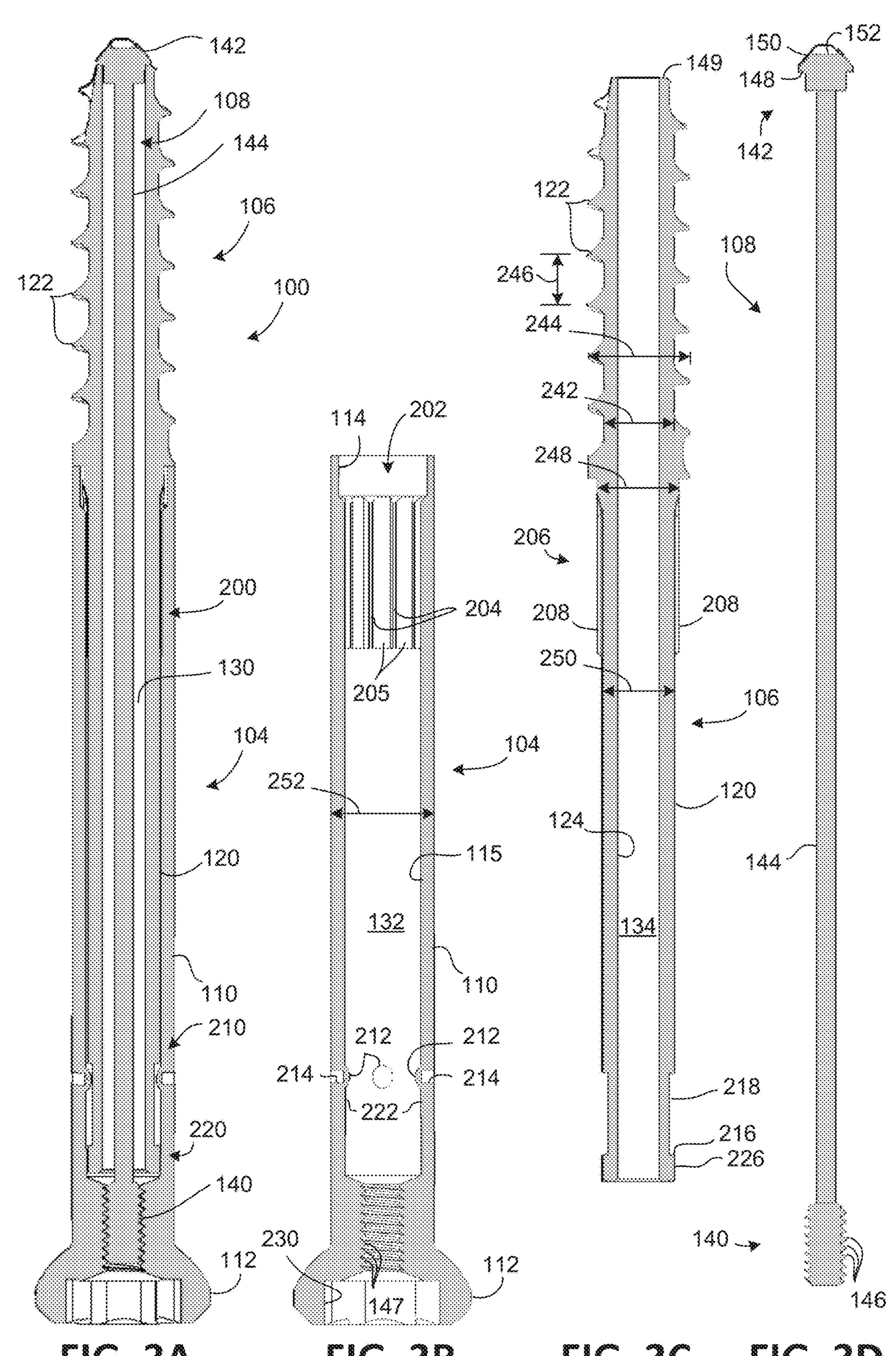
FIGS. 3A, 3B, 3C, and 3D are side elevation, section views of the bone screw, the proximal member, the distal member, and the tension member, respectively, of FIG. 1.

As shown more clearly in FIGS. 2 and 3A, the bone screw 100 may be assembled by, first, inserting the proximal end 140 of the tension member 108 along the proximal direction, through the open distal end of the distal member 106, until the distal flange 148 of the distal end 142 of the tension member 108 rests against the corresponding surface 149 of the distal member 106. Then, the distal shank 120 of the distal member 106 and the proximal end 140 of the tension member 108 may be inserted into the proximal portion 132 of the variable-length cavity 130, within the proximal member 104. The tension member 108 may be rotated relative to the proximal member 104 and the distal member 106 (for example, by rotating the distal tip 150 of the tension member 108 with a flat-head screwdriver or other driver) such that the proximal threads 146 of the proximal end 140 of the tension member 108 engage the interior threads 147 of the proximal member 104.

This may result in the configuration shown in FIG. 3A, in which the tension member 108 resides generally within the variable-length cavity 130, which is defined by the proximal member 104 and the distal member 106. The variable-length cavity 130 may include a proximal portion 132 within the proximal member 104, and a distal portion 134 within the distal member 106. Part of the distal portion 134 may also reside within the proximal member 104, as the distal shank 120 is within the proximal portion 132 of the variable-length cavity 130.

The bone screw 100 may be used for a variety of purposes, including but not limited to fracture fixation, joint arthrodesis, and implant fixation. In some implementations, the bone screw 100 may be inserted through one bone portion or implant, and into a separate bone portion in which the bone-engaging threads 122 are anchored. As mentioned previously, in some embodiments, the bone screw 100 may be inserted into a pilot hole previously formed in the bone. In alternative embodiments, the bone screw 100 may be driven against the bone to form and tap its own hole.

In either case, the bone screw 100 may be rotated (for example, via a driver) such that the bone-engaging threads 122 draw the bone screw 100 to advance until the head 112 rests against the exterior surface of the proximal bone portion or implant. Then, the bone screw 100 may be further advanced such that the distal member 106 is urged distally, by virtue of the action of the bone-engaging threads 122, relative to the proximal member 104. The tension member 108 may be dimensioned such that the shank 144 of the tension member 108 elongates in response to this force, permitting the distal member 106 to move distally while the proximal member 104 remains generally in place.

The tension on the shank 144 may cause the tension member 108 to exert compressive force, drawing the distal member 106 back proximally relative to the proximal member 104. This compressive force may act across the junction between the bone portions (or in the case of implant fixation, between the bone and the implant), and may beneficially facilitate osteointegration, fracture healing, lasting fracture fixation, and/or the like.

This further advancement of the distal member 106 may continue until the bone screw 100 has reached its desired length. The length may be selected such that the tension member 108 continues to exert compressive force, even after some of the strain in the tension member 108 has relaxed, for example due to bone subsidence, patient motion, and/or other factors.

In some embodiments, the proximal member 104 and the distal member 106 may be formed of relatively high-strength biocompatible materials such as titanium and/or titanium alloys. The tension member 108 may advantageously be formed of a biocompatible superelastic material such as Nitinol. The superelastic material may beneficially undergo considerable strain while exerting a generally constant compressive force on the proximal member 104 and the distal member 106. Thus, the tension member 108 may maintain compression even after some relaxation in strain has occurred.

The bone screw 100 will likely be under considerable stress as it is driven into the bone and/or as the patient goes about his or her activities with the bone screw 100 in place. In a larger screw (such as most wood screws), these stresses may not be of concern. However, the bone screw 100 may desirably be relatively small in diameter—for example, from 3.5 mm to 7.0 mm, measured at the diameter of the proximal shank 110 of the proximal member 104. The bone screw 100 may thus have a number of features that help distribute, shift, and/or otherwise manage stresses in the proximal member 104, the distal member 106, and/or the tension member 108 to avoid failure (for example, breakage or plastic deformation) of the proximal member 104, the distal member 106, and/or the tension member 108. Notably, hollow screws of this size that lack such stress distribution features may be likely to fail during insertion and/or during healing.

More specifically, the bone screw 100 may have a torque transmission feature, a length limiting mechanism, a bending transmission feature, and deliberately selected exterior diameter. Each of these features may help to control some aspect of the stresses experienced by the proximal member 104, the distal member 106, and/or the tension member 108, as will be described below.

The bone screw 100 may have a torque transmission feature that transmits torque from the proximal member 104 to the distal member 106. The torque transmission feature may be configured to control stresses in the proximal member 104 and the distal member 106 incident to application of torque as the bone screw 100 is driven into the bone. It has been observed that torque transmission features with torque transmission surfaces oriented circumferentially, or nearly circumferentially, can be subject to high hoop stresses as these surfaces, as can the surfaces to which they transmit torque. Conventional polyhedral interfaces (such as a hexagonal hole and driver) are thus subject to high stresses during torque transmission. Similarly, an interface in which one or more flats on a cylindrical member are placed within a hole having one or more matching flats, would also be subject to high stress.

Accordingly, the torque transmission feature employed by the bone screw 100 may have a design in which the torque transmission surface(s) are angled significantly from the circumferential direction. This angle may be greater than 20°, greater than 30°, greater than 40°, greater than 50°, greater than 60°, greater than 70°, or even greater than 80°. In some embodiments, the angle may be 90°. Further, in other embodiments, this angle may be even greater than 90°. Although large angles may be beneficial for hoop stress reduction, in some embodiments, sufficient hoop stress reduction may be obtained with torque transmission surfaces that are angled such that they are oriented closer to the radial direction than the circumferential direction.

As embodied in FIGS. 1A through 5, and shown most clearly in FIG. 4, the torque transmission feature of the bone screw 100 may be a spline 200. The spline 200 may include an outer spline component 202 formed on the proximal interior surface 114 of the proximal member 104, and an inner spline component 206 formed on the distal shank 120 of the distal member 106. The outer spline component 202 may mesh with the inner spline component 206 such that the outer spline component 202 transmits torque to the inner spline component 206. Thus, as the proximal member 104 is rotated by the surgeon (for example, via a driver engaging the head 112), the distal member 106 may also rotate, driving the bone-engaging threads 122 into the bone.

As further shown in FIG. 4, the outer spline component 202 may have torque transmitting surfaces 203 that are on the leading sides of outer teeth 204 as the proximal member 104 rotates about the longitudinal axis 102, along the direction of rotation R. The outer teeth 204 may extend along part of the length of the proximal portion 132 of the variable-length cavity 130, parallel to the longitudinal axis 102. The outer teeth 204 may be separated from each other by outer grooves 205 that also extend parallel to the longitudinal axis 102.

The outer spline component 202 is shown with ten of the outer teeth 204; however, those of skill in the art will recognize that any number of teeth may be present. In some embodiments, only a single tooth may be present. The presence of multiple teeth may help to spread the loads induced by torque transmission across additional surfaces, and to multiple sectorial portions of the proximal member 104 and the distal member 106.

The inner spline component 206 may have torque receiving surfaces 207 that are on the trailing surfaces of inner teeth 209 as the distal member 106 rotates about the longitudinal axis 102, along the direction of rotation R. The inner teeth 209 may extend along part of the length of the distal portion 134 of the variable-length cavity 130, parallel to the longitudinal axis 102. The inner teeth 209 may be separated from each other by inner grooves 208 that also extend parallel to the longitudinal axis 102.

The number of inner grooves 208 on the inner spline component 206 may be equal to the number of outer teeth 204 on the outer spline component 202. In FIG. 4, there are ten of the outer teeth 204 that reside within ten of the inner grooves 208. Similarly, there are ten of the inner teeth 209 that reside within ten of the outer grooves 205. Thus, the outer spline component 202 meshes with the inner spline component 206. As indicated previously, more or fewer teeth or grooves may be present in either component. The number of teeth in one component may be equal to the number of grooves in the other, but this is not necessarily the case—in some embodiments, unequal numbers of teeth and/or grooves may be present between inner and outer spline components.

The torque transmitting surfaces 203 of the outer spline component 202 may advantageously be angularly displaced from the circumferential direction C by an angle Φ, shown in FIG. 4. The line L represents one of the torque transmitting surfaces 203 of the outer spline component 202. As set forth above, the angle Φ may be significant so as to reduce hoop stresses in the proximal member 104 and/or the distal member 106. In some embodiments, the angle Φ may be greater than an angle θ between the line L and the radial direction R. Thus, the angle Φ may be greater than 45°.

The spline 200 represents only one of multiple different types of torque transmission features that may be used within the scope of the present disclosure. Various other torque transmission features, including but not limited to polyhedral and curvilinear shapes, may be used. A polyhedral torque transmission feature may include star shapes, rectangles, and/or other shapes with torque transmission surfaces that are angularly displaced from the circumferential direction. Curvilinear torque transmission features may likewise have such angled torque transmission surfaces, and may include curvilinear and/or rectilinear segments. In some embodiments, a more organically-shaped rounded spline may be used. In other embodiments, an ovoid, elliptical, or other curvilinear torque transmission feature may be present.

The bone screw 100 may also have a length limiting mechanism 210 that helps to control the elongation of the bone screw 100. Unlimited elongation of the bone screw 100 may cause the tension member 108 to fail in tension, as the loads experienced by the tension member 108 (static and/or fatigue loading) may cause the tension member 108 to break or plastically deform. In some embodiments, the length limiting mechanism 210 may operate to limit the displacement of the distal member 106 relative to the proximal member 104 such that the stress on the tension member 108 remains within its superelastic zone, as will be shown and described hereafter. Further, in some embodiments, the bone screw 100 may be designed for infinite life. Thus, the length limiting mechanism 210 may be designed to limit displacement of the distal member 106 relative to the proximal member 104 such that the strength limits of the tension member 108 are not exceeded.

As shown, the length limiting mechanism 210 may include a proximal stop feature on the proximal member 104 and a distal stop feature on the distal member 106. The proximal stop feature and the distal stop feature may come into contact with each other when the maximum length of the bone screw 100 is reached, preventing further distal motion of the distal member 106 relative to the proximal member 104. The proximal stop feature and the distal stop feature may each take many forms. One or more than one of each of the proximal stop feature and the distal stop feature may be present in a bone screw according to the present disclosure.

As shown in FIGS. 3A, 3B, and 5, the proximal member 104 may have multiple proximal stop features, each of which is a protrusion 212 on the proximal interior surface 114. Each protrusion 212 may protrude inwardly (i.e., toward the longitudinal axis 102 and the distal member 106, nested within the proximal portion 132 of the variable-length cavity 130) from the remainder of the proximal interior surface 114. Each protrusion 212 may be formed, for example, through the use of apertures 214 formed in the exterior surface of the proximal member 104. In some embodiments, the apertures 214 may be formed as blind holes that are separated from the proximal portion 132 of the variable-length cavity 130 by relatively thin walls. After the distal shank 120 of the distal member 106 has been inserted into the proximal portion 132 of the variable-length cavity 130, pins or other projecting members may be inserted into the apertures 214 and pressed inwardly to flex the thin walls inward, thus forming each protrusion 212.

The distal member 106 may have a single distal stop feature that contacts all of the protrusions 212. As shown in FIGS. 3A, 3C, and 5, the distal stop feature of the distal member 106 may be a shoulder 216 that defines one end of a relief 218 formed on the distal shank 120 of the distal member 106. Specifically, the relief 218 may be formed as a smaller-diameter section of the distal shank 120, on an extension of the distal shank 120 that extends proximally from the inner spline component 206. The relief 218 may be proximate a proximal end of the distal shank 120 and may define the shoulder 216.

After full insertion of the distal shank 120 into the proximal portion 132 of the variable-length cavity 130, the relief 218 may be aligned with the apertures 214 of the proximal member 104. Thus, when the protrusions 212 are formed as described above, the protrusions 212 may extend inwardly into the relief 218. The protrusions 212 may protrude sufficiently into the relief 218 such that the shoulder 216 is unable to move distally beyond the protrusions 212. Thus, abutment of the shoulder 216 against the protrusions 212 may limit the extent to which the distal member 106 is able to move distally relative to the proximal member 104.

When the distal shank 120 is fully inserted into the proximal portion 132 of the variable-length cavity 130 (such that the distal shank 120, in its entirety, is received within the proximal portion 132), the protrusions 212 may reside near the distal end of the relief 218. Thus, the length of the relief 218 may define the extent to which the distal member 106 is able to move distally relative to the proximal member 104.

Advantageously, the length limiting mechanism 210 may be displaced proximally of the spline 200. Thus, the length limiting mechanism 210 may operate without interfering with operation of the spline 200, and without requiring added complexity in the torque transmission feature of the bone screw 100.

A "length limiting mechanism" may include any of a wide variety of devices that can limit the elongation of a bone screw. Similarly, a "proximal motion stop" and a "distal motion stop" may each include any feature that can be physically interfere with such elongation. Thus, proximal and distal motion stops may include any known combination of protruding elements, including but not limited to flanges, bumps, tabs, detents, shoulders, and the like. Such elements may protrude inwardly, outwardly, and/or in a circumferential direction.

The bone screw 100 may also have a bending transmission feature 220 that helps to transfer bending loads between the proximal member 104 and the distal member 106 at a location displaced from where such loading is applied. For example, if the bone screw 100 is inserted through a first bone portion such that the bone-engaging threads 122 anchor in a second bone portion, motion (or attempted motion) of the user may urge the second bone portion to move relative to the first bone portion. This force may be in shear (i.e., urging relative motion parallel to the interface or fracture between the first and second bone portions), tension (urging relative motion perpendicular to the interface or fracture), bending (urging relative motion along an axis offset from the longitudinal axis 102 of the bone screw 100), and/or torsion (urging rotation of the second bone portion relative to the first bone portion about the longitudinal axis 102 of the bone screw 100).

These forces may result in a bending moment on the bone screw 100 and may be greatest at the interface between the first and second bone portions. The bending transmission feature 220 may advantageously be displaced proximally or distally from this interface and may thus distribute some of these forces away from the interface. Further, the bending transmission feature 220 may transfer some bending load from the distal member 106 to the proximal member 104. The distal member 106 may have the smaller cross-sectional shape proximate the interface between the first and second bone portions and may thus be subject to higher bending stress. Accordingly, shifting some of this bending stress to the proximal member 104 may increase the overall bending load that can be tolerated by the bone screw 100.

As shown in FIGS. 3A, 3B, and 3C, the bending transmission feature 220 may include a proximal engagement surface 222 on the proximal member 104 and a distal engagement surface 226 on the distal member 106. In the embodiment of FIGS. 3A, 3B, and 3C, the distal engagement surface 226 may be an outwardly-facing surface proximal to the shoulder 216, at the proximal end of the distal shank 120. The proximal engagement surface 222 may be located on a proximal portion of the interior surface 115, which faces inwardly, and faces the distal engagement surface 226.

The distal engagement surface 226 may be sized such that it has a diameter near that of the proximal engagement surface 222. Advantageously, the distal engagement surface 226 may be slightly smaller than the proximal engagement surface 222 such that the distal engagement surface 226 can be received within the proximal engagement surface 222 with clearance during assembly of the proximal member 104 and the distal member 106. This clearance may be relatively small so that, in response to slight bending of the bone screw 100, the distal engagement surface 226 abuts the proximal engagement surface 222 to transmit some of the bending load from the distal member 106 to the proximal member 104.

For example, a bending load on the bone screw 100 may urge the distal member 106 to shift such that its axis is no longer colinear with the axis of the proximal member 104. This motion of the distal member 106 may cause the distal shank 120 of the distal member 106 to move toward one side of the interior surface 115. Abutment of the distal engagement surface 226 with the proximal engagement surface 222 may limit this bending such that the material near the maximum bending stress (for example, near the interface between bone portions) is not stressed at a level that would cause it to plastically deform or break.

The bending transmission feature 220 is only one of many possible structures that may be used to transmit bending loads away from the site of maximum stress. Notably, the bone screw 100 may include other features that may also act as bending transmission features, in addition to or in the alternative to the proximal engagement surface 222 and the distal engagement surface 226. Any surfaces of the proximal member 104 and the distal member 106 that abut each other in response to application of bending load on the bone screw 100 may be considered bending transmission features. In particular, the entire length of the distal shank 120 (with the exception of the relief 218) proximal to the inner spline component 206, and the corresponding inwardly-facing regions of the interior surface 115 of the proximal member 104, may also act as bending transmission features, as they may abut each other and transmit bending loads from the distal member 106 to the proximal member 104 as the bone screw 100 is loaded in bending.

Further, the phrase "bending transmission feature" includes any combination of surfaces, however shaped, that abut each other to transmit such loading. By way of example and not limitation, such surfaces may have cylindrical, splined, polygonal, irregular, and/or other cross-sectional shapes. Such surfaces may be parallel to the longitudinal axis 102, or in alternative embodiments, may be angled nonparallel to the longitudinal axis 102. Thus, bending transmission features need not be linear extrusions, but may instead have conical, semispherical, or other shapes with variation toward and/or away from the longitudinal axis 102.

The bone screw 100 may further have other features and/or dimensions that help provide the bone screw 100 with enhanced strength and/or rigidity over prior art variable-length screws. For example, many known screws have a shank that is only as large as the minor diameter of the screw threads. Such a design has the benefit of simple preparation, as the corresponding pilot hole may be formed with a drill bit (not shown) with a constant diameter. By contrast, the bone-engaging threads 122 of the bone screw 100 may be dimensioned such that portions of the bone screw 100 proximal to the bone-engaging threads 122 (excluding the head 112) are larger than the minor diameter of the bone-engaging threads 122.

Specifically, as shown in FIG. 3C, the bone-engaging threads 122 may have a minor diameter 242, a major diameter 244, and a pitch 246. The distal shank 120 may have an exterior diameter 248, adjacent to the bone-engaging threads 122, that is larger than the minor diameter 242 of the bone-engaging threads 122. This may provide the distal shank 120, and in particular, the portion of the distal shank 120 adjacent to the bone-engaging threads 122, with added bending strength over that which would be present in bone screws with shanks that are limited in size to the minor diameter of the screw threads.

The distal shank 120 may also have an exterior diameter 250, displaced proximally of the bone-engaging threads 122, and also proximal to the inner spline component 206. The exterior diameter 250 may also be larger than the minor diameter 242 of the bone-engaging threads 122. In some embodiments, the exterior diameter 248 and/or the exterior diameter 250 may be equal to and/or larger than the major diameter 244. In yet other embodiments, the exterior diameter 248 and/or the exterior diameter 250 may be the equal in size, larger, or smaller than the average of the minor diameter 242 and the major diameter 244 of the bone-engaging threads 122.

As a result of these deliberate dimensioning decisions, the weakest cross-section of the bone screw 100, as to bending, may be displaced from the location of maximum bending stress. More precisely, maximum bending stress may be experienced at the interface between the items being secured together by the bone screw 100 (for example, between two bone fragments or portions to be secured together). A screw (not shown) with distal threading with a minor diameter equal to the outer diameter of the shank of the screw may have a weakest cross section, as to bending, displaced significantly proximally of the screw threads. Thus, the location of maximum stress may unfortunately align with the part of the screw that is most susceptible to bending, which may be near the center of the screw.

Conversely, the bone screw 100 may have a weakest cross section, as to bending, that is distal to the center of the screw, and thus likely displaced distally of the location of maximum bending stress. For example, the weakest cross section of the bone screw 100, as to bending, may be immediately proximal to the bone-engaging threads 122. This location may be displaced distally from the interface between bone portions when the bone screw 100 is fully inserted because the bone-engaging threads 122 may advantageously be driven fully into the distal bone portion or fragment, and then driven further to cause elongation of the bone screw 100, as will be described hereafter.

Further, as shown in FIG. 3B, the proximal shank 110 may have an exterior diameter 252 that is also larger than the minor diameter 242 of the bone-engaging threads 122. Thus, not only the distal member 106, but also the proximal member 104, may have enhanced strength and/or rigidity. As further shown in FIG. 3A, the exterior diameter 252 may be as large as the major diameter 244 of the bone-engaging threads 122, providing the bone screw 100 with yet more additional strength and/or rigidity. In alternative embodiments, the exterior diameter 252 may be larger than the minor diameter 242 but smaller than the major diameter 244 of the bone-engaging threads 122.

The exterior diameter 252 may conform to standard or otherwise known sizes for orthopedic screws. This may facilitate use of the bone screw 100 in place of conventional screws for a wide variety of orthopedic applications. In some embodiments, the exterior diameter 252 may be within the range of 1 mm to 10 mm. Yet more specifically, the exterior diameter 252 may be within the range of 2 mm to 8 mm. Still more specifically, the exterior diameter 252 may be within the range of 3.5 mm to 7 mm. In some embodiments, the exterior diameter 252 may be within the range of 4 mm to 6 mm. Yet more specifically, the exterior diameter 252 may be about 5 mm. FIGS. 1A through 5 are shown to scale for the particular embodiment of the bone screw 100; hence, other dimensions of the bone screw 100 may be derived from these possible values of the exterior diameter 252.

The bone screw 100 may be applied to bone and/or implant structures in a wide variety of ways. In some embodiments, a pilot hole may first be formed in the bone in which the bone-engaging threads 122 are to be engaged. A stepped pilot drill bit (not shown) may advantageously be used for this purpose. The stepped pilot drill bit may have a distal portion with a smaller diameter and a proximal portion with a larger diameter. The distal portion may have a length and position that corresponds to the location of the bone-engaging threads 122 when the bone screw 100 has been fully inserted and/or when the bone-engaging threads 122 have reached their final position in the bone.

Figure 6A:
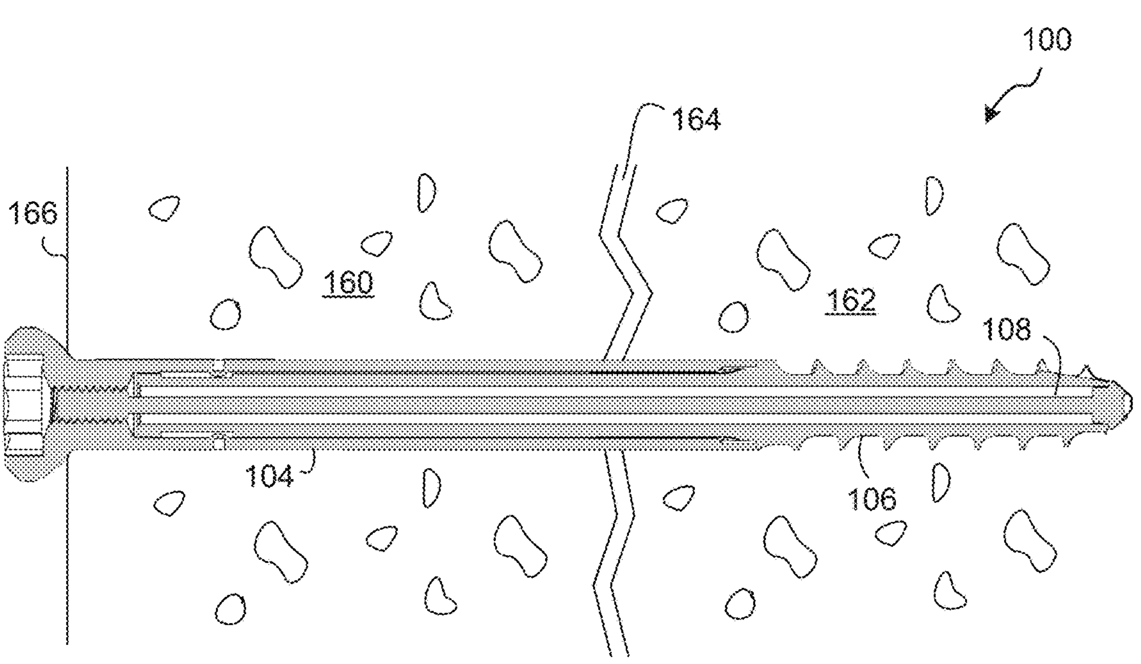
FIGS. 6A and 6B are side elevation, section views of the bone screw of FIG. 1, upon initial insertion into bone, and upon further insertion to tension the bone screw, respectively.
Figure 6B:
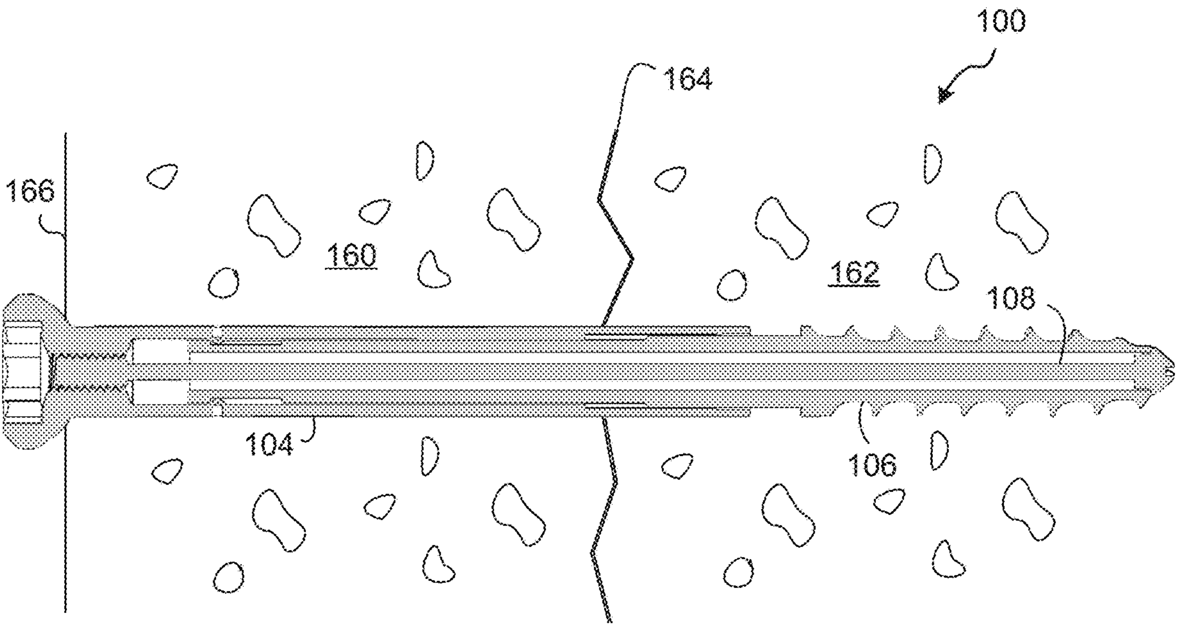

FIGS. 6A and 6B are side elevation, section views of the bone screw 100 of FIG. 1, upon initial insertion into bone, and upon further insertion to tension the bone screw, respectively. As shown, the bone screw 100 may be used, in this particular implementation, to secure a first bone portion 160 to a second bone portion 162. The first bone portion 160 and the second bone portion 162 may be fragments of a single fractured bone, or they may be previously separate bone structures that are to be brought together and fused and/or otherwise secured to each other.

As shown, the first bone portion 160 and the second bone portion 162 may initially be separated from each other by an interface 164, at which a gap exists between the first bone portion 160 and the second bone portion 162. The first bone portion 160 may be nearer the surgeon and may have an exterior cortex 166.

The bone screw 100 may first be inserted into the pilot hole. In order to reach the position shown in FIG. 6A, torque may be applied to the head 112 of the bone screw 100 such that the bone-engaging threads 122 engage the second bone portion 162. Torque may continue to be applied until the head 112 seats on the exterior cortex 166 of the first bone portion 160 as shown.

With the head 112 seated against the exterior cortex 166, further torque may be applied to the bone screw 100 in order to drive the bone-engaging threads 122 further into the second bone portion 162 and draw the second bone portion 162 toward the first bone portion 160, closing the gap at the interface 164. Leaving the bone screw 100 in this configuration may hold the second bone portion 162 and the first bone portion 160 together for a period of time, but once stress is applied to the first bone portion 160 and the second bone portion 162, or once bone proximate the interface 164 begins to subside, a gap may form again at the interface 164.

Thus, further torque may be applied to the bone screw 100 to cause the bone screw 100 to elongate, applying compression between the first bone portion 160 and the second bone portion 162 even after such motion and/or subsidence occurs. More specifically, elongation of the bone screw 100 may occur as the shank 144 of the tension member 108 elongates, resulting in the configuration shown in FIG. 6B. The tension member 108, in turn, may pull the distal member 106 back toward the proximal member 104, compressing the second bone portion 162 against the first bone portion 160. Such compression may continue as long as the tension member 108 is elongated. Use of a superelastic material to form the tension member 108 may help provide a continuous level of compression between the first bone portion 160 and the second bone portion 162 as the bone screw 100 shortens, rather than providing a high level of compression at maximum elongation, followed by lesser compression as the bone screw 100 is permitted to shorten due to motion of the first bone portion 160 and the second bone portion 162, or due to subsidence.

As discussed previously, the length of the bone screw 100, and therefore the compression applied by the tension member 108 and the compression applied by the tension member 108, may be limited by the operation of the length limiting mechanism 210. Thus, as the bone screw 100 reaches the length shown in FIG. 6B, the protrusions 212 of the proximal member 104 may abut the shoulder 216 of the distal member 106 to prevent further elongation of the bone screw 100. This limitation may help to ensure that the tension member 108 does fail in tension and does not apply excessive compression across the interface 164.

The configuration of the bone screw 100 may help control the manner in which torque is applied to the bone screw 100 to insert and then elongate the bone screw 100. A threshold torque may be required to cause the bone screw 100 to elongate; this threshold torque may generally be higher than the level of torque required to drive the bone screw 100 into the first bone portion 160 and the second bone portion 162, up until the head 112 contacts the exterior cortex 166 of the first bone portion 160.

Figure 7:
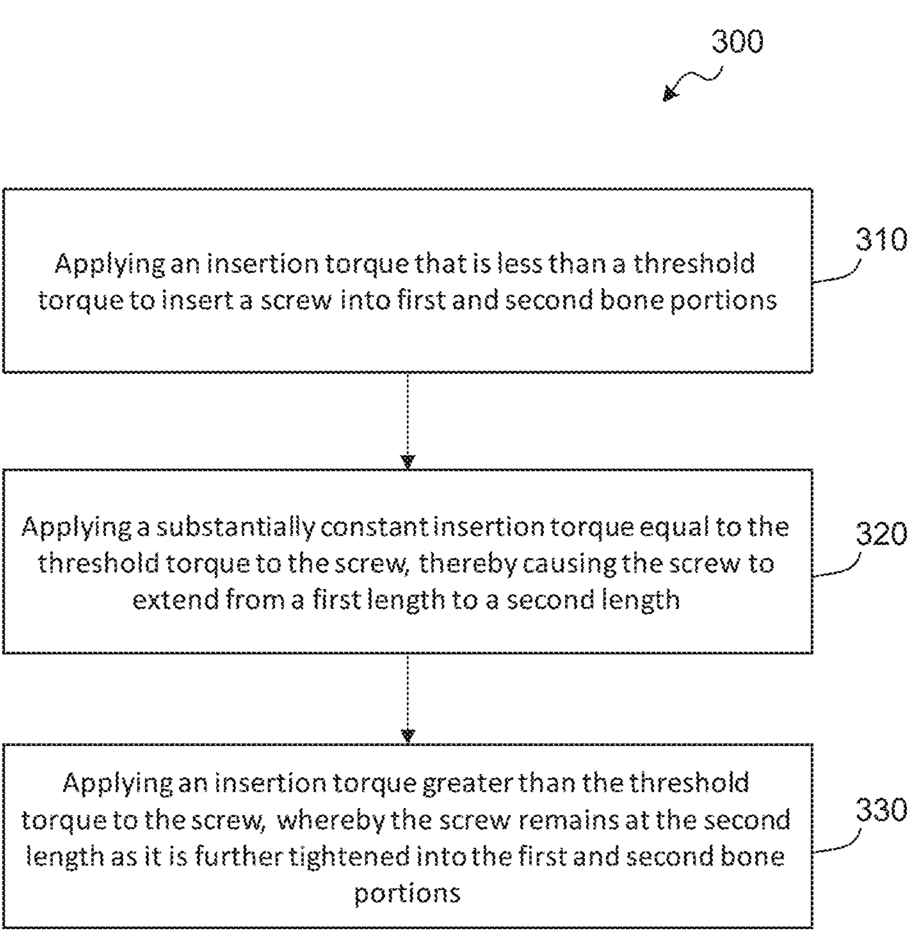
FIG. 7 is a flowchart depicting a method of inserting a bone screw into bone, according to one embodiment.

FIG. 7 is a flowchart depicting a method 300 of inserting the bone screw 100 into bone, according to one embodiment. As shown, the method 300 may commence with a step 310 in which an insertion torque is applied to the bone screw 100. As mentioned above, this insertion torque may be less than the threshold torque required to cause elongation of the bone screw 100. The step 310 may continue until the head 112 seats against the exterior cortex 166.

The method 300 may then proceed to a step 320 in which further torque is applied, at a level equal to the threshold torque required to elongate the bone screw 100, until the bone screw 100 is fully elongated. Use of a superelastic, material (such as Nitinol) in the tension member 108 may cause the threshold torque to remain generally constant as the bone screw 100 elongates. This is distinct from conventional materials, which may require an increasing level of tension (and therefore increasing torque) as strain in the material increases.

Once the bone screw 100 has elongated fully, the method 300 may proceed to a step 330 in which an insertion torque is again applied at a higher level than the threshold torque as the bone screw 100 is further tightened in the first bone portion 160 and the second bone portion 162. This tightening may not further elongate the bone screw 100, which may be at its maximum length. However it may, for example, seat the head 112 deeper in the exterior cortex 166 and apply additional compression across the interface 164 between the first bone portion 160 and the second bone portion 162.

The bone screw 100 may not be designed for insertion along a guide wire. Full assembly of the bone screw 100 prior to insertion may interfere with use of a guide wire, as the tension member 108 may occupy the variable-length cavity 130 that would otherwise receive the guide wire. However, in alternative embodiments, a bone screw may be designed for insertion along a guide wire and subsequent assembly, and elongation, in-situ. One such embodiment will be shown and described subsequently in connection with FIGS. 11 through 17.

Figure 8:
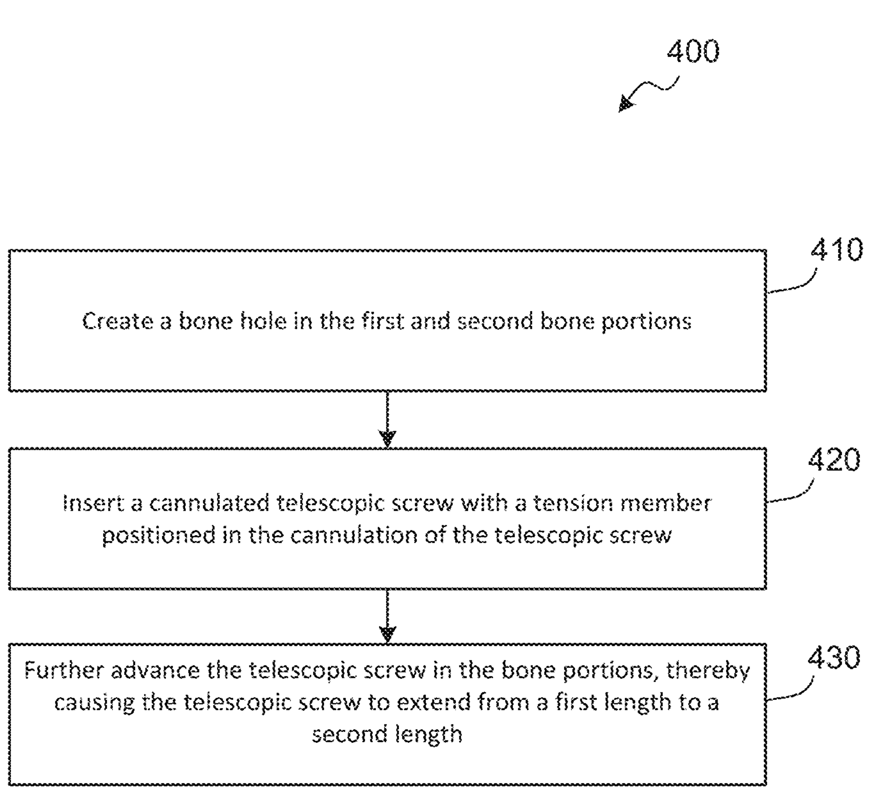
FIG. 8 is a flowchart depicting a method of inserting a bone screw into bone along a guide wire, according to one embodiment.

FIG. 8 is a flowchart depicting a method 400 of inserting a bone screw, such as the bone screw 100 of FIGS. 1A through 5, into bone according to one embodiment. The method 400 assumes that the bone screw 100 is used to secure two bone portions (for example, two fragments of a single bone to be repaired, or two bones to be locked together); similar methods may be envisioned for use of the bone screw 100 to secure an implant to bone.

As shown, the method 400 may commence with a step 410 in which a bone hole is formed in the first and second bone portions. As mentioned previously, this may be done with a stepped pilot drill bit (not shown) that forms a smaller hole in the second bone portion 162, and a larger hole in the first bone portion 160. In alternative embodiments, the bone screw 100 may be self-tapping, and the step 410 may be omitted.

The method 400 may proceed to a step 420 in which the bone screw 100, in a fully-assembled state (including the tension member 108), is inserted into the holes formed in the first bone portion and in the second bone portion 162. This may be done without using a guide wire. Insertion of the bone screw 100 may be carried out by rotating the bone screw 100 with a driver (not shown) until the head 112 of the bone screw 100 abuts the exterior cortex 166 of the first bone portion 160 (the proximal bone portion).

In a step 430, the bone screw 100 may be further advanced, causing the bone screw 100 to extend from a first length to a second length. The first length may be the base (unelongated) length of the bone screw 100, as shown in FIG. 6A. The second length may be the fully extended length of the bone screw 100, as shown in FIG. 6B. In the alternative, the second length may less than the maximum length of the bone screw 100. Elongation of the bone screw 100 pursuant to the step 430 may be carried out by further rotating the bone screw 100 with the driver such that the distal member 106 moves distally relative to the proximal member 104. This rotation may be carried out until the bone screw 100 has reached the second length.

After performance of the step 430, the tension member 108 may be under tension, and may exert compressive force urging the distal member 106 to move proximally back toward the proximal member 104. This compressive force may be propagated to the interface 164 between the first bone portion 160 and the second bone portion 162 to accelerate healing and/or fusion.

Those of skill in the art will recognize that the method 300 of FIG. 7 and the method 400 of FIG. 8 may be performed with other extendable bone screws besides the bone screw 100 of FIGS. 1A through 5. Further, the bone screw 100 may be used in connection with surgical methods besides the method 300 and the method 400.

Returning to the bone screw 100 of FIGS. 1A through 5, as mentioned previously, the tension member 108 may be formed of a superelastic material such as Nitinol. The manner in which this affects performance of the bone screw 100 will be further shown and described in connection with FIG. 9A.

Figure 9A:
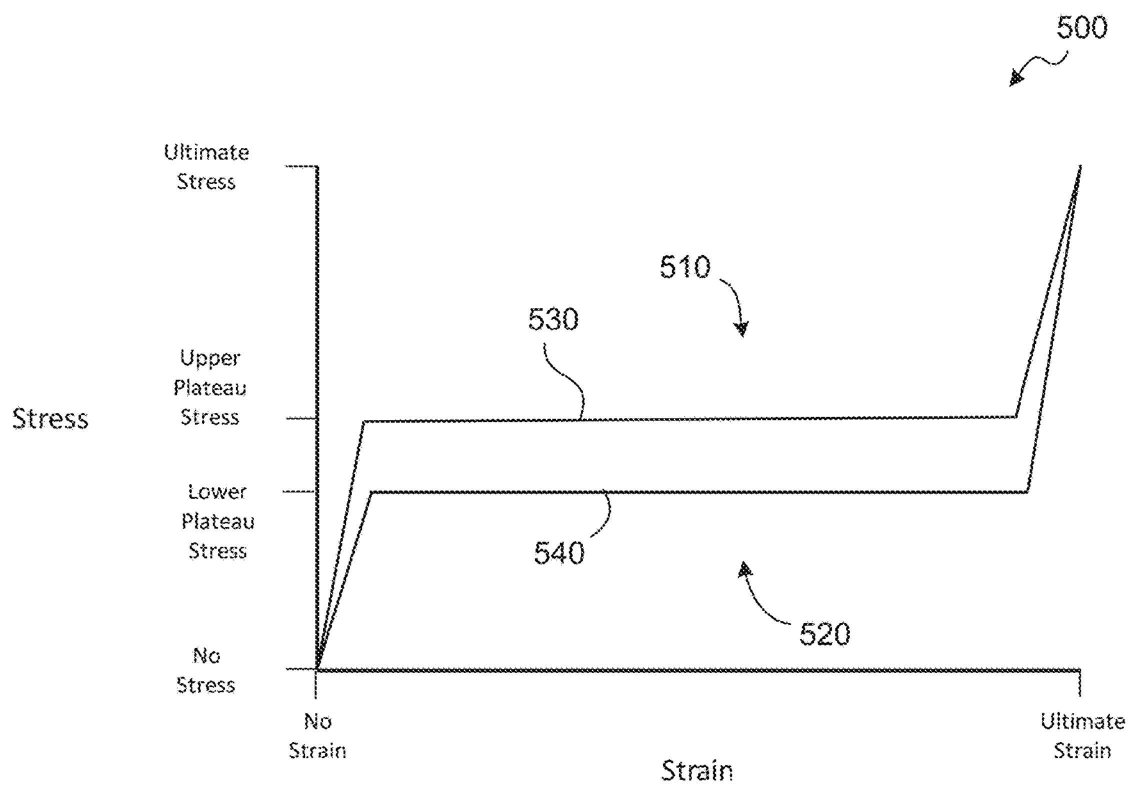
FIG. 9A is a diagram depicting stress versus strain for an exemplary superelastic material.

FIG. 9A is a diagram 500 depicting stress versus strain for an exemplary superelastic material. The diagram 500 is idealized and is only meant to indicate general properties of superelastic materials.

As shown, the diagram 500 may have a strain curve 510, showing stress versus strain under increasing stress, and a recovery curve 520, showing stress versus strain as stress is reduced. The strain curve 510 may have a horizontal portion 530, showing that the material will undergo steadily increasing strain as an upper plateau stress is applied. The strain range represented by horizontal portion 530 is referred to herein as superelastic strain. The strain at the left end of horizontal portion 530 represents the beginning of the transition of the superelastic material from a first crystal structure phase such as austenite to a second crystal structure phase such as martensite. The right end of horizontal portion 530 represents the complete transformation to the second crystal structure phase, and this represents the limit of superelastic strain. The span between the left and right ends of horizontal portion 530 is referred to herein as the superelastic zone. This upper plateau stress may be the stress experienced by the tension member 108 as the threshold level of torque is applied. The horizontal portion 530 may be generally horizontal, showing that application of torque at the threshold level (rather than at an increasing level) will cause the tension member 108 to continue to elongate.

The recovery curve 520 may also have a horizontal portion 540, showing that the material will undergo a steadily reducing strain, while a constant level of stress is maintained. This shows the performance of the bone screw 100 as the bone screw 100 is permitted to shorten again, due to shifting of the first bone portion 160 and the second bone portion 162 and/or subsidence of the first bone portion 160 and/or the second bone portion 162. The strain level experienced by the tension member 108 may equate to the compressive force applied by the bone screw 100, urging the first bone portion 160 and the second bone portion 162 together. The length and horizontal orientation of the horizontal portion 540 indicate how relatively steady compression at the lower plateau stress level may be maintained even as considerable shortening of the bone screw 100 occurs. Thus, the bone screw 100 may maintain compression to help the first bone portion 160 and the second bone portion 162 to heal and/or fuse, even while the bone screw 100 is shorter than its maximum length at the time of surgery.

Figure 9B:
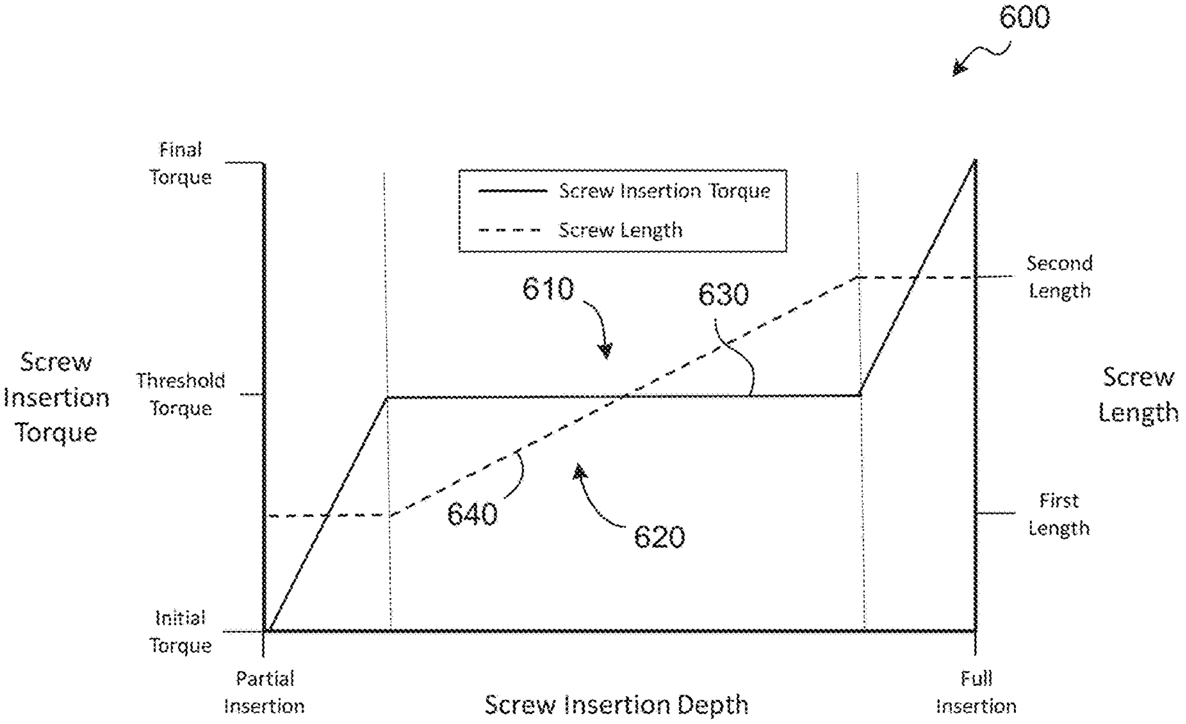
FIG. 9B is a diagram depicting changes in insertion torque and screw length during screw insertion.

FIG. 9B is a diagram 600 depicting changes in insertion torque and screw length during screw insertion. A torque curve 610 depicts the torque needed to advance the bone screw 100. A length curve 620 shows the length of the bone screw 100. The torque curve 610 may rise gradually and then level off at the threshold torque one the bone screw 100 has been fully inserted and begins to elongate. A horizontal portion 630 of the torque curve 610 may indicate how the insertion torque remains relatively constant during elongation of the bone screw 100. In the length curve, this elongation is shown by a flat portion 640 with a constant upward slope. Prior to application of the threshold torque, and after the bone screw 100 reaches its maximum length, the length curve 620 is horizontal, reflecting a lack of change in length of the bone screw 100.

Figure 10A:
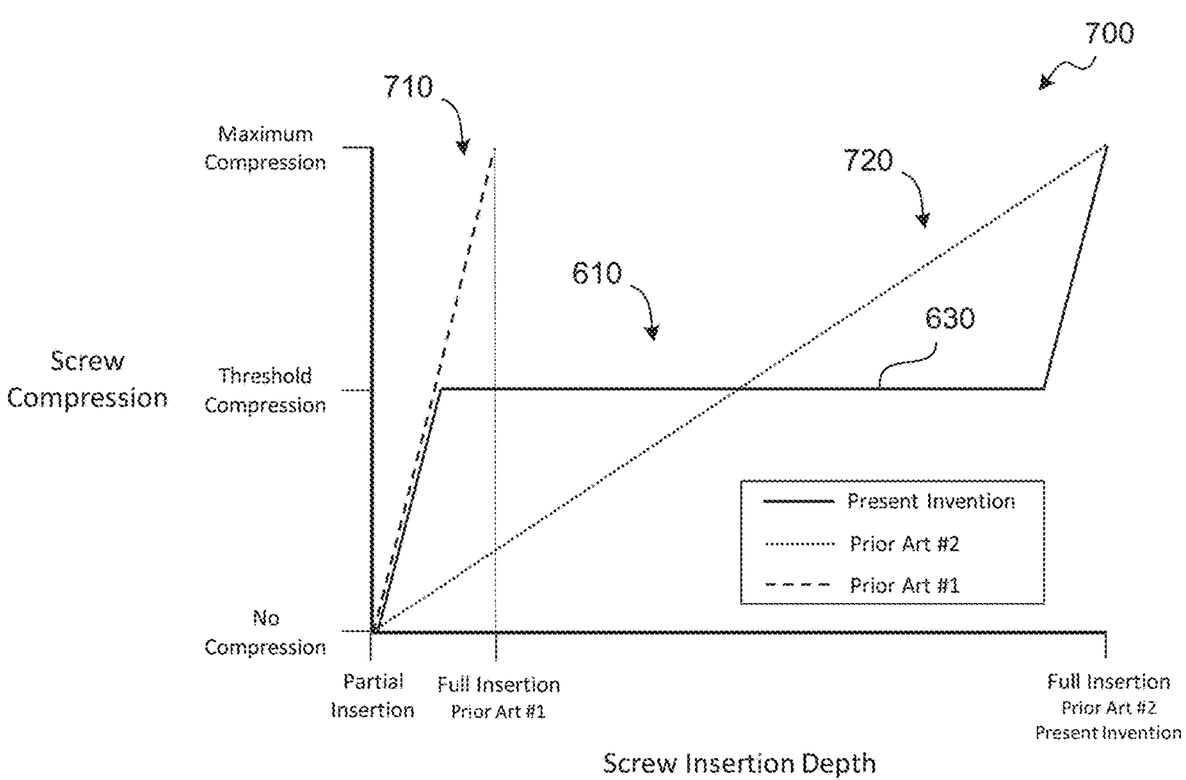
FIG. 10A is a diagram depicting changes in screw compression during screw insertion.

FIG. 10A is a diagram 700 depicting changes in screw compression during insertion of the bone screw 100, as in FIG. 9B. The torque curve 610 is compared with a torque curve 710 for "Prior Art #1," which is a standard bone screw that does not elongate, and a torque curve 720 for "Prior Art #2," which is a bone screw with elongation provided by a more conventional coil spring that is not formed of a superelastic material.

As shown, the torque curve 710 has a constant slope, which is relatively steep, reflecting the fact that a conventional bone screw does not elongate significantly. The insertion depth of the screw is thus limited by the excessively high torque required to deepen insertion of the screw, and the correspondingly high tension applied to the screw (and compression applied across the interface 164). Excessive torque may cause the screw to fail during insertion, and excessive compression may cause the bone to fail. Accordingly, insertion depth is limited, and any subsidence or motion in the first bone portion 160 and/or the second bone portion 162 may be expected to negate compression across the interface 164.

The torque curve 720 also has a constant slope, which is less steep than that of the torque curve 710. This reflects the elongation provided by the coil or other conventional spring, which provides greater elongation than a conventional screw, but still requires increasing torque to obtain greater insertion depth. Again, any relative motion and/or subsidence in the first bone portion 160 and/or the second bone portion 162 may reduce the elongation in the spring, causing the compression applied across the interface between bone portions to decrease in proportion to the slope of the torque curve 720. This concept will be further illustrated in FIG. 10B.

Figure 10B:
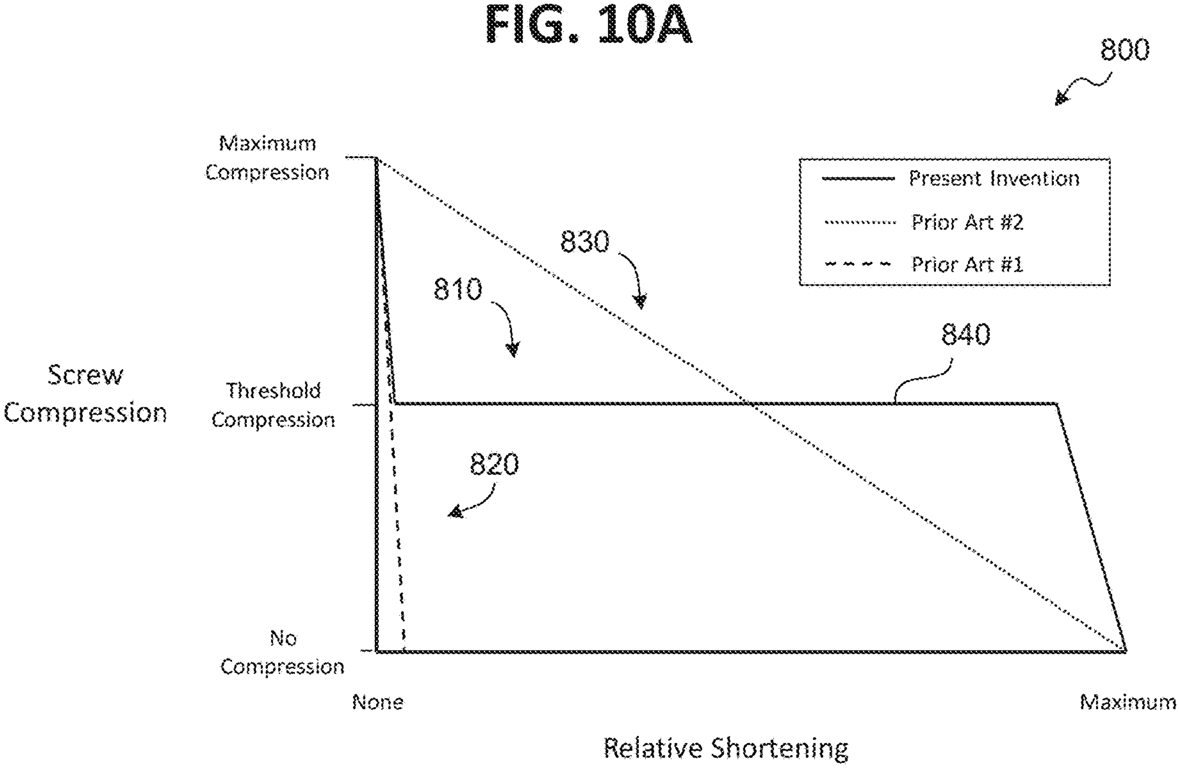
FIG. 10B is a diagram depicting changes in screw decompression during relative shortening between bone portions.
Figures 11A, 11B, 11C, 11D:
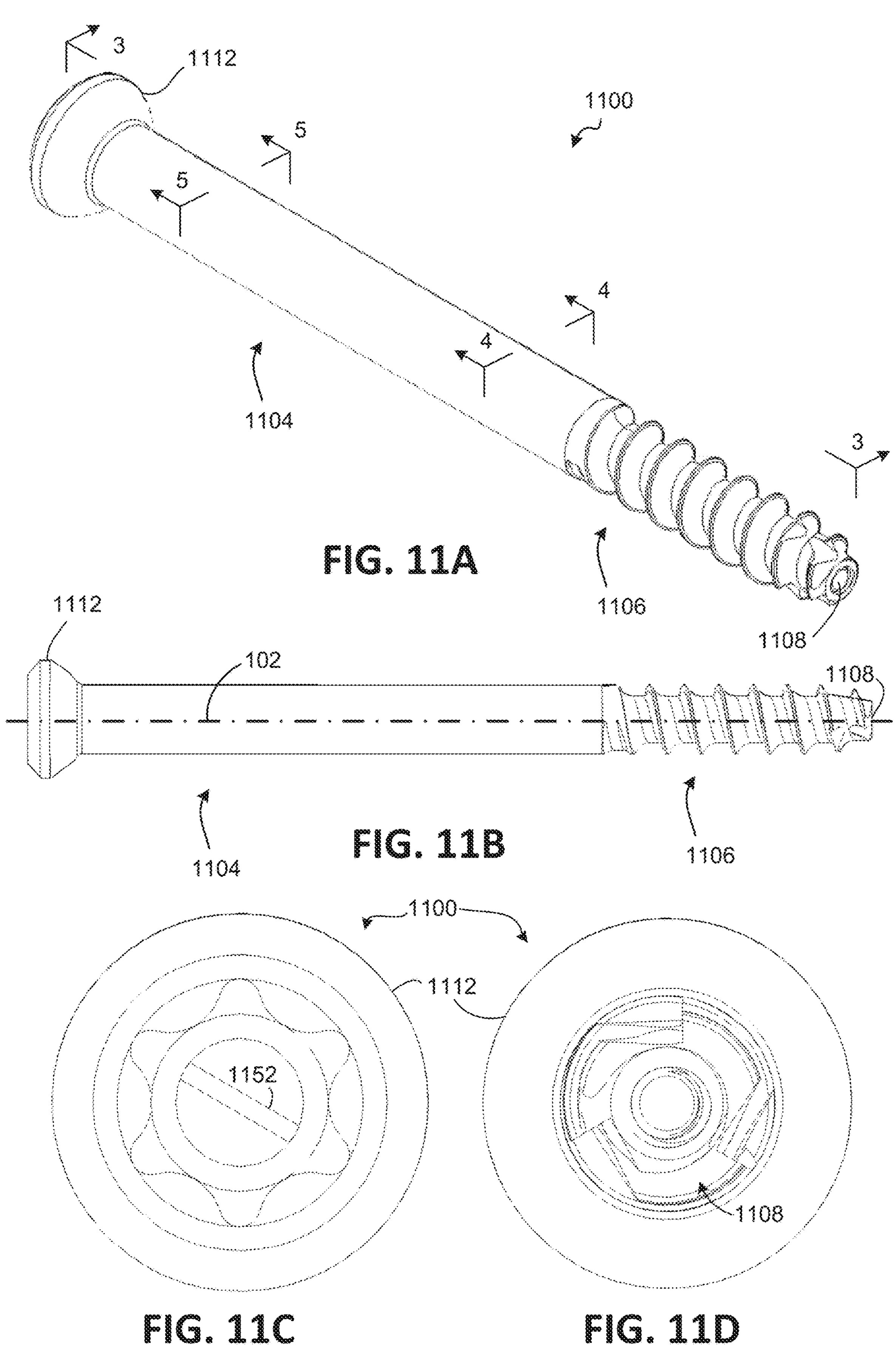
FIGS. 11A, 11B, 11C, and 11D are perspective, side elevation, front elevation, and rear elevation views, respectively, of a bone screw according to another embodiment.

FIG. 10B is a diagram 800 depicting changes in screw decompression during relative shortening between bone portions. A decompression curve 810 is shown for the bone screw 100, as well as a decompression curve 820 for Prior Art #1 and a decompression curve 830 for Prior Art #2. The decompression curve 820 and the decompression curve 830 illustrate how compression applied across the interface 164 between the first bone portion 160 and the second bone portion 162 decreases in response to shortening of the bone screw. The decompression curve 810 may have a horizonal portion 840.

With the conventional bone screw, only a minimal amount of strain in the screw needs to be relieved before all compression across the interface 164 is lost. With the bone screw with a conventional spring, relief of strain reduces the compression across the interface 164 in relation to the slope of the decompression curve 830, which may be the inverse of the slope of the torque curve 720 of the diagram 700. Accordingly, the only way to maintain an optimal level of compression across the interface 164 (for example, a level of compression close to the "Threshold Compression" of FIG. 10B) with this screw is to apply excessive compression at the time of surgery, so that strain relief only reduces the compression applied by the screw down from the excessive compression level to the healthy compression level. As mentioned previously, application of excessive compression (i.e., by applying high torque to the screw) can result in failure of the screw and/or the surrounding bone.

By contrast, the decompression curve 810 illustrates how a broad range of strain relief in the bone screw 100 can occur without significantly changing the level of compression applied across the interface 164. The bone screw 100 need not be torqued excessively in order to accomplish this. Rather, the bone screw 100 may advantageously be inserted only far enough to remain in the horizonal portion 840 of the decompression curve 810. In some embodiments, the horizonal portion 840 may extend across a length of 0 to 5 mm. More precisely, the horizonal portion 840 may extend across a length of 1 to 4 mm. Still more precisely, the horizonal portion 840 may extend across a length of 1.5 to 3 mm. Yet more precisely, the horizonal portion 840 may extend across a length of 2 mm.

This concept may apply across all of FIGS. 9A, 9B, 10A, and 10B. For example, with reference to FIG. 9A, the tension member 108 of the bone screw 100 may be tensioned only enough that the stress and strain experienced by the tension member 108 remains in the horizontal portion 530 of the strain curve 510. This limit may be provided by the length limiting mechanism 210, which may limit elongation of the tension member 108 during insertion of the bone screw 100 to keep stress in the tension member 108 from moving beyond (i.e., to the right of) the horizontal portion 530. Relief of stress in the tension member 108 may thus only traverse the horizontal portion 540 of the recovery curve 520. This is reflected in FIG. 9B, in which further torque applied to the bone screw 100 after the bone screw 100 has traversed the horizontal portion 630 of the torque curve 610, may not cause further elongation of the bone screw 100. All of this may be transparent to the surgeon, who can simply drive the screw in a generally conventional manner.

The bone screw 100 of FIGS. 1A through 5 is only one of many embodiments of the present disclosure. Those of skill in the art will recognize that many variations could be conceived. For example, in some embodiments, the bone-engaging threads 122 may be adapted for the type of bone being penetrated. This may entail use of more or fewer bone-engaging threads 122, or bone-engaging threads 122 with different shapes and/or sizes, than those depicted in FIGS. 1A through 5. In other embodiments, the proximal member 104 and the distal member 106 may be reconfigured such that the proximal member (not shown) has a distal end that resides within the proximal end of the distal member (not shown). Further, as set forth above, a wide variety of torque transmission features, length limiting mechanisms, bending transmission features, driver engagement features, and/or the like may be used, in addition to or in place of those of the bone screw 100.

Figure 17:
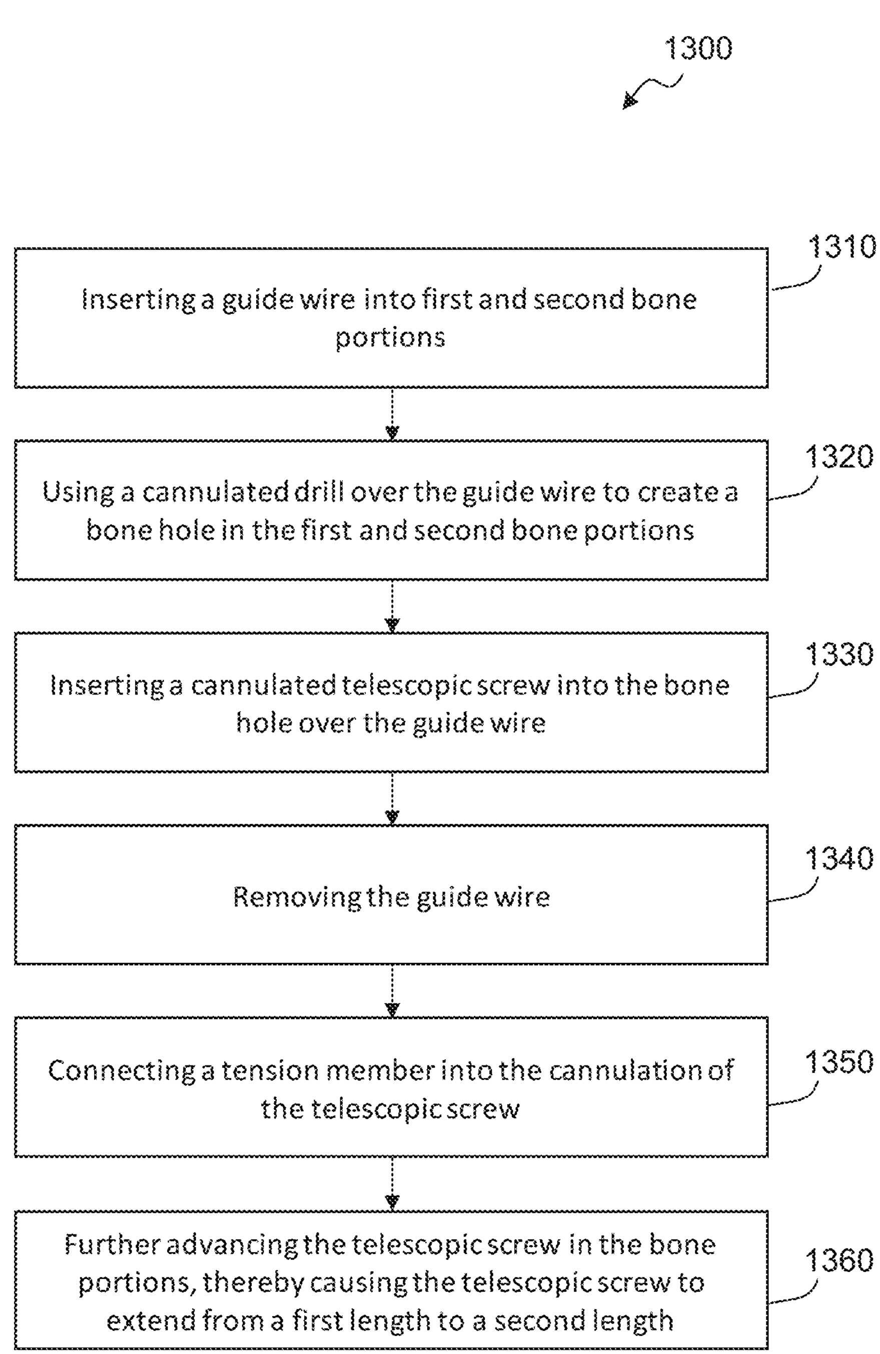
FIG. 17 is a flowchart depicting a method of inserting a bone screw into bone, according to another embodiment.

In some embodiments, it may be desirable to use a variable-length bone screw in conjunction with a guide wire, as will be set forth in the method 1300 of FIG. 17. FIGS. 11A through 15 show a bone screw 1100 that is configured to facilitate use with a guide wire.

Figure 12:
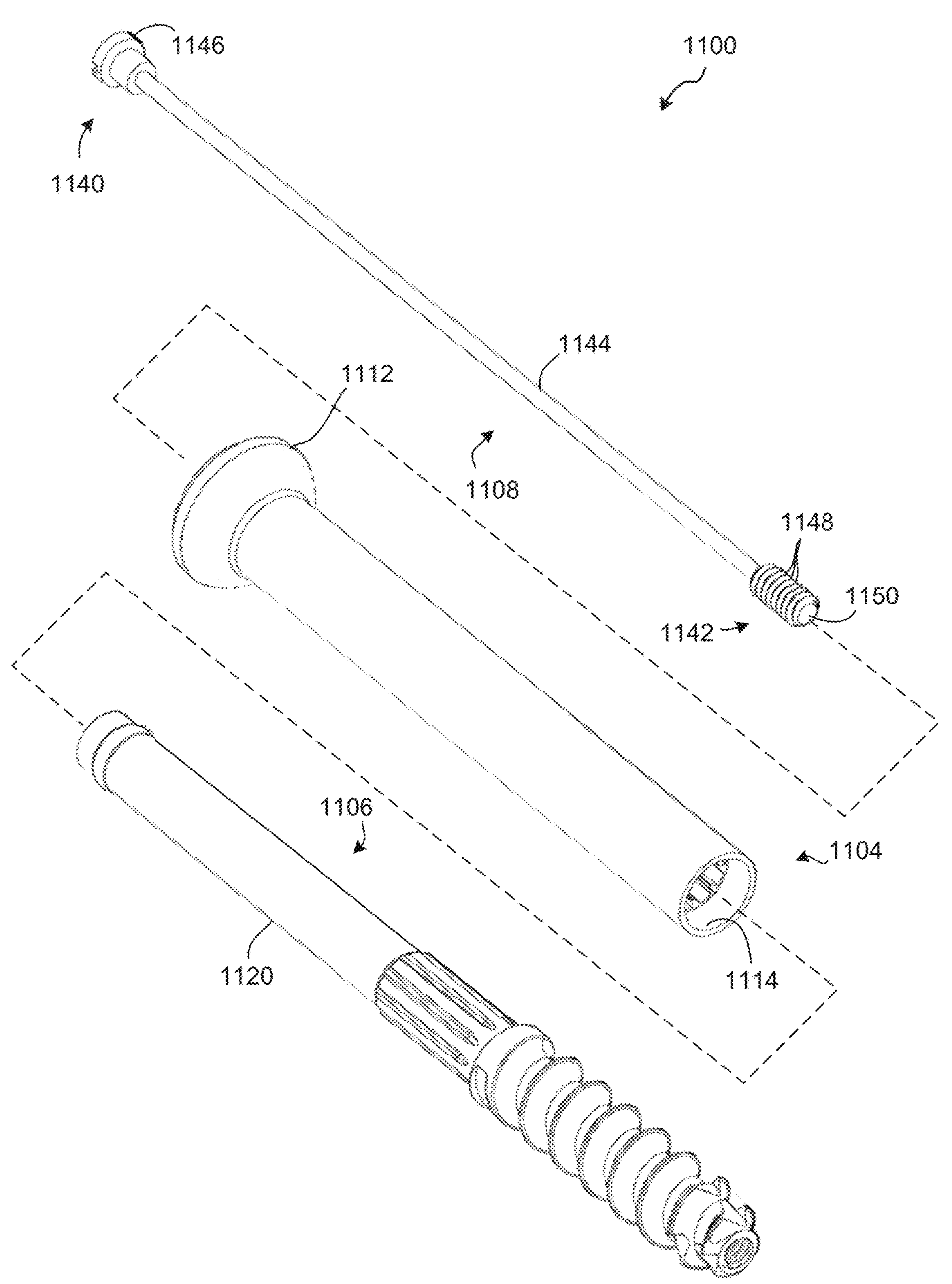
FIG. 12 is an exploded, perspective view of the bone screw of FIG. 11.
Figures 13A, 13B, 13C, 13D:
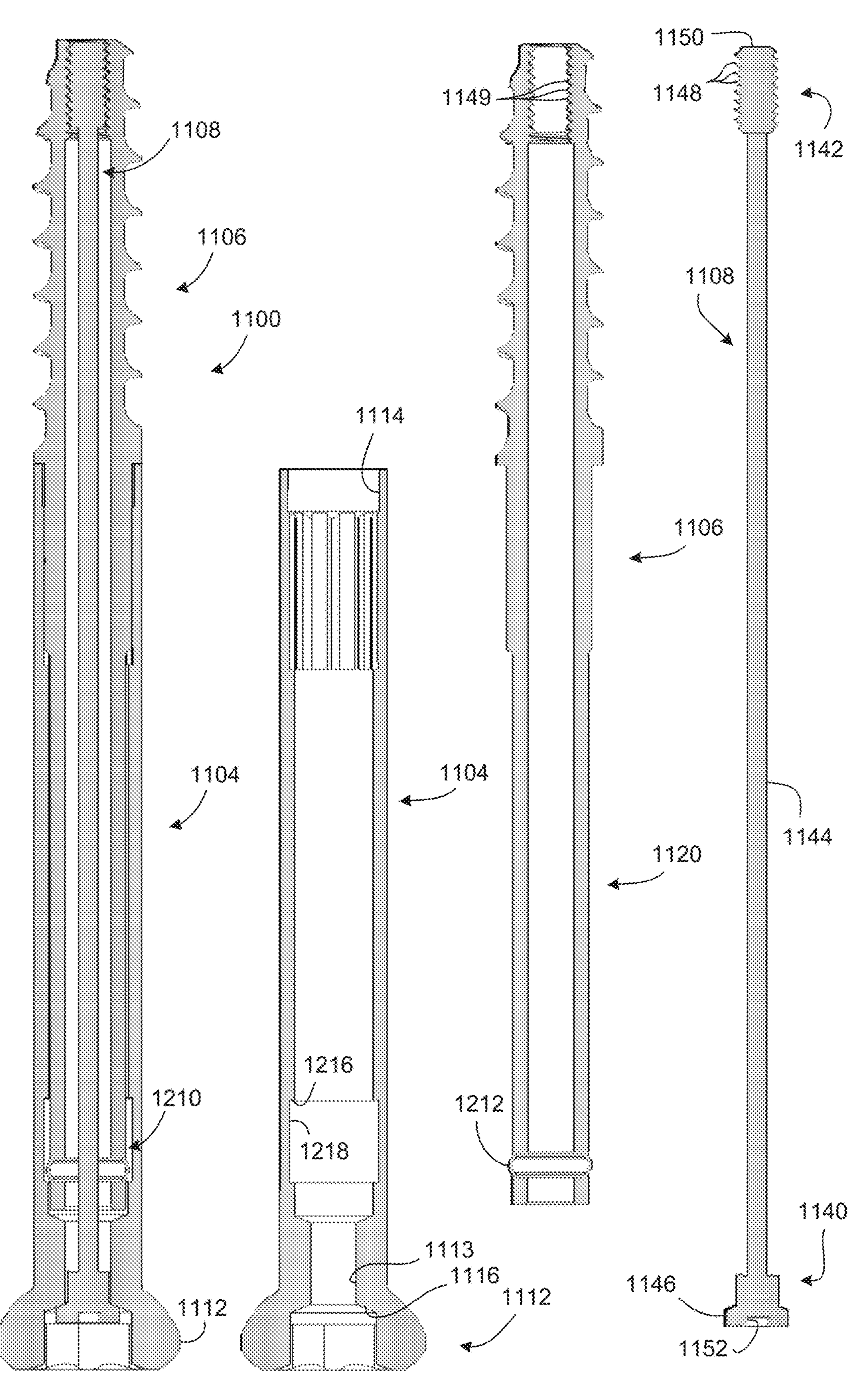
FIGS. 13A, 13B, 13C, and 13D are side elevation, section views of the bone screw, the proximal member, the distal member, and the tension member, respectively, of FIG. 11.
Figure 14:
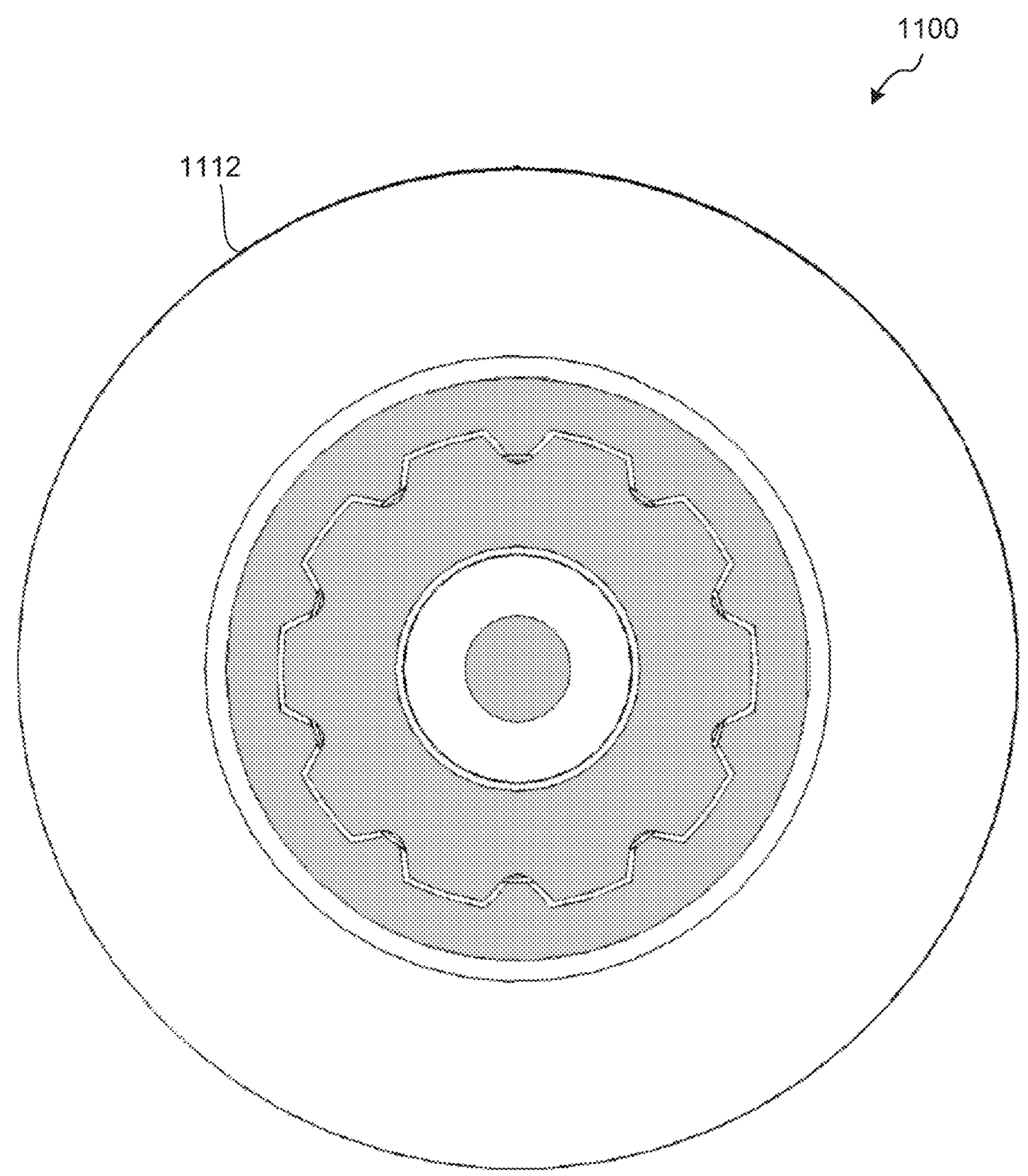
FIG. 14 is a front elevation, section view of the bone screw of FIG. 11.
Figure 15:
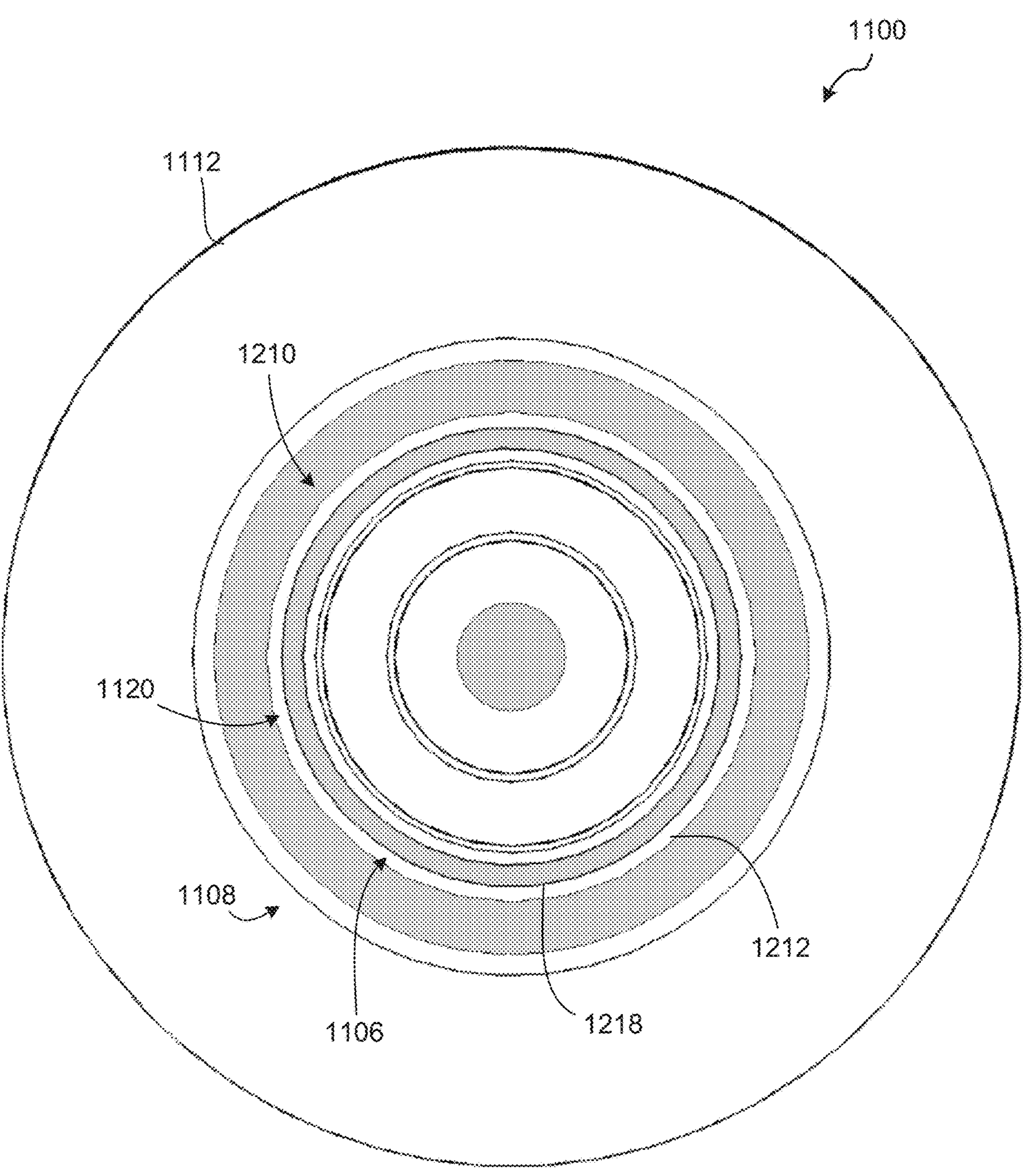
FIG. 15 is another front elevation, section view of the bone screw of FIG. 11.

The bone screw 1100 may have a longitudinal axis 102, a proximal member 1104, a distal member 1106, and a tension member 1108. FIGS. 11A, 11B, 11C, and 11D are perspective, side elevation, front elevation, and rear elevation views, respectively, of the bone screw 1100. FIG. 12 is an exploded, perspective view of the bone screw 1100. FIGS. 13A, 13B, 13C, and 13D are side elevation, section views of the bone screw 1100, the proximal member 1104, the distal member 1106, and the tension member 1108, respectively. FIG. 14 is a front elevation, section view of the bone screw 1100. FIG. 15 is another front elevation, section view of the bone screw 1100. Various parts of the bone screw 1100 may be identical or similar to their counterparts on the bone screw 100; they will not be described again here. All statements made regarding the bone screw 100 apply to the bone screw 1100, unless they would be contradicted by the differences between the two.

The bone screw 1100 may be configured to allow the tension member 1108 to be inserted into the proximal member 1104 and the distal member 1106 after the remainder of the bone screw 1100 (i.e., the proximal member 1104 and the distal member 1106) have been assembled together and inserted into the bone. The tension member 1108 may be designed to be inserted into and coupled to the proximal member 1104 and the distal member 1106 after the proximal member 1104 and the distal member 1106 have been implanted in the bone.

Specifically, like the tension member 108 of the bone screw 100 of FIGS. 1A through 5, the tension member 1108 may have a proximal end 1140, a distal end 1142, and a shank 1144, extending along the longitudinal axis 102, that connects the proximal end 1140 to the distal end 1142. However, in place of the proximal threads 146 of the tension member 108, the proximal end 1140 of the tension member 1108 may have a head 1146 that is wider than the shank 1144. The proximal member 104 may have a head 1112 with an aperture 1113 leading into the interior of the proximal member 1104, defining a surrounding shoulder 1116 on which the head 1146 of the tension member 1108 can rest.

The distal end 1142 may have distal threads 1148 that facilitate coupling of the tension member 1108 to the distal member 1106 engagement of the distal threads 1148 with interior threads 1149 of the distal member 1106. The distal end 142 may further have a distal tip (not shown) that is sufficiently sharp for bone penetration, or alternatively, may have a distal tip 1150, as shown, that is blunt, as the distal tip 1150 need not penetrate the bone because the tension member 1108 may not be inserted into the bone until after penetration has already been performed via formation of the pilot hole and/or insertion of the distal member 1106 into the bone.

The head 1146 may have one or more driver engagement features that are operable independently of the driver engagement feature 230 of the head 1112. For example, the head 1146 may have a slot 1152 (shown in FIG. 11C) that facilitates rotation of the tension member 1108 with a driver such as a flat-head screwdriver.

In use, the proximal member 1104 and the distal member 1106 may be assembled and driven into the bone over a guide wire, as will be set forth in the method 1300 of FIG. 17. Then the guide wire may be removed, and the tension member 1108 may be inserted into the proximal member 1104 and the distal member 1106 by inserting the distal end 1142 through the aperture 1113, through the proximal member 1104, and into the distal member 1106 such that the distal threads 1148 of the distal end 1142 reach the interior threads 1149 of the distal member 1106. A driver may be used to rotate the tension member 1108, causing the distal threads 1148 to engage the interior threads 1149. When the distal threads 1148 have been fully received in the interior threads 1149, the head 1146 of the proximal end 1140 of the tension member 1108 may rest on the shoulder 1116 of the head 1112 of the proximal member 1104, preventing further distal motion of the head 1146.

With the tension member 1108 in place within the proximal member 1104 and the distal member 1106, the bone screw 100 may be further driven into the bone to move the distal member 1106 distally relative to the proximal member 1104, causing the tension member 1108 to elongate. The head 1146 of the tension member 1108 may continue to press against the shoulder 1116 of the proximal member 1104 as the interior threads 1149 of the distal member 1106 move distally.

Like the bone screw 100, the bone screw 1100 may have a length limiting mechanism 1210 that controls the extent to which the bone screw 1100 can increase in length. The length limiting mechanism 1210 may function in a manner similar to that of the length limiting mechanism 210 of the bone screw 100.

Specifically, the length limiting mechanism 1210 may have a distal stop feature and a proximal stop feature that engage each other when the distal member 1106 has reached its maximum displacement relative to the proximal member 1104 to prevent further distal motion of the distal member 1106 relative to the proximal member 1104. The distal stop feature may be a protrusion 1212 on a distal shank 1120 of the distal member 1106. The protrusion 1212 may extend radially outwardly, away from the longitudinal axis 102 of the bone screw 1100. The proximal stop feature may be a shoulder 1216 defined at the distal end of a relief 1218 formed in a proximal interior surface 1114 of the proximal member 1104. The protrusion 1212 may extend radially into the relief 1218 such that distal motion of the distal member 1106 causes the protrusion 1212 to abut the shoulder 1216, arresting further distal motion of the distal member 1106 relative to the proximal member 1104.

Figure 16A:
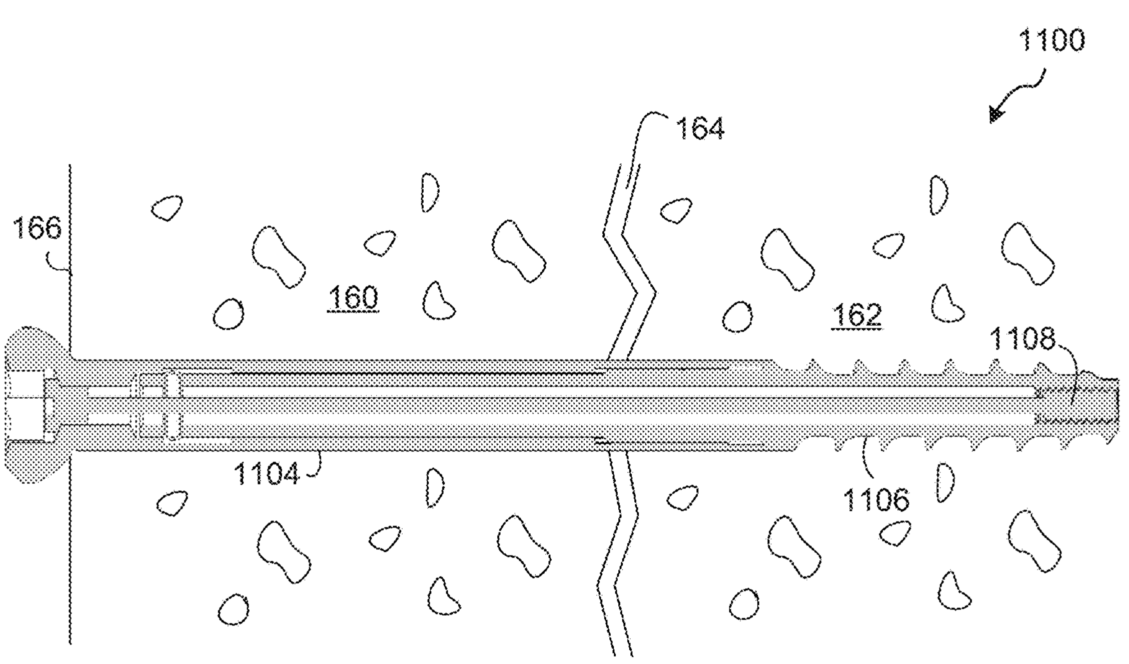
FIGS. 16A and 16B are side elevation, section views of the bone screw of FIG. 11, upon initial insertion into bone, and upon further insertion to tension the bone screw, respectively.
Figure 16B:
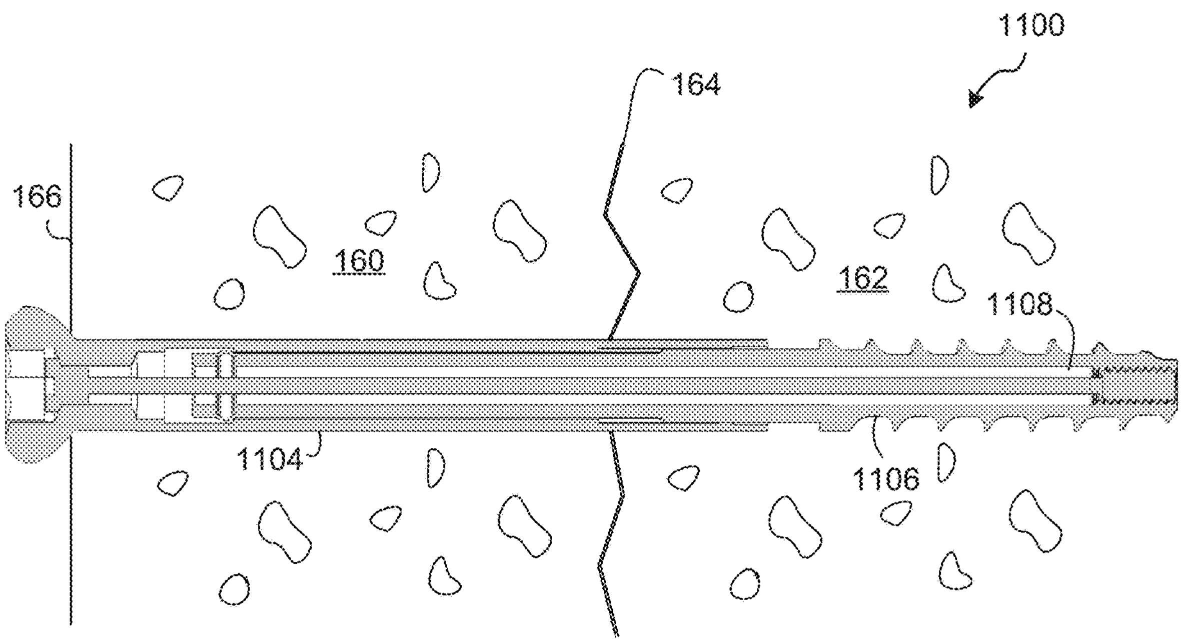

FIGS. 16A and 16B are side elevation, section views of the bone screw 1100 of FIG. 11, upon initial insertion into bone, and upon further insertion to tension the bone screw, respectively. FIG. 16A may depict the bone screw 1100 immediately after performance of the step 1350 of the method 1300 of FIG. 17, i.e., after the tension member 1108 has been inserted into and coupled to the proximal member 1104 and the distal member 1106, but before further torque has been applied to the bone screw 1100 to drive the distal member 1106 further into the second bone portion 162. FIG. 16B may depict the bone screw 1100 after performance of the step 1360 of the method 1300 of FIG. 17, after the bone screw 1100 has been elongated to its maximum length. Again, the interface 164 has been closed by the compression applied between the first bone portion 160 and the second bone portion 162 by the bone screw 1100 in its elongated form.

Notably, the bone screw 100 and the bone screw 1100 may not always be elongated to their maximum lengths. In some embodiments, it may be beneficial to stop applying torque to the bone screw 100 and/or the bone screw 1100 before maximum length has been reached.

FIG. 17 is a flowchart depicting a method 1300 of inserting a bone screw into bone along a guide wire, according to one embodiment. As shown, the method 1300 may commence with a step 1310 in which the guide wire is inserted into the two bone portions, such as the first bone portion 160 and the second bone portion 162 of FIGS. 6A and 6B, at the desired location for the bone screw. Then the method 1300 may proceed to a step 1320 in which a cannulated drill (for example, with a stepped diameter as mentioned above), is inserted over the guide wire and used to form the pilot hole at the desired location.

With the pilot hole formed, the method 1300 may proceed to a step 1330 in which the bone screw is inserted over the guide wire, without the tension member. The bone screw may partially or fully inserted into the bone at this stage, with the guide wire in place. The step 1330 may be similar to the step 310 of the method 300. Then, in a step 1340, the guide wire may be removed, leaving the variable-length cavity of the bone screw vacant.

In a step 1350, the tension member may be inserted into the variable-length cavity of the bone screw, and connected to the proximal and distal members of the bone screw to undergo tension as the screw elongates. Then, in a step 1360, further torque may be applied to the fully-assembled bone screw so that the bone screw elongates and places the tension member under tension, as in the step 320 of the method 300. Optionally, in a further step (not shown), further torque may be applied to the bone screw, as in the step 330 of the method 300.

Notably, in some alternative embodiments, an elongating bone screw may have a head designed to embed partially or fully in the proximal bone portion. In such embodiments, threading may be provided on the screw head. One such example will be shown and described in connection with FIG. 18.

Figure 18:
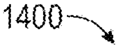
FIG. 18 is a side elevation view of a bone screw according to yet another embodiment.
Figure 18:
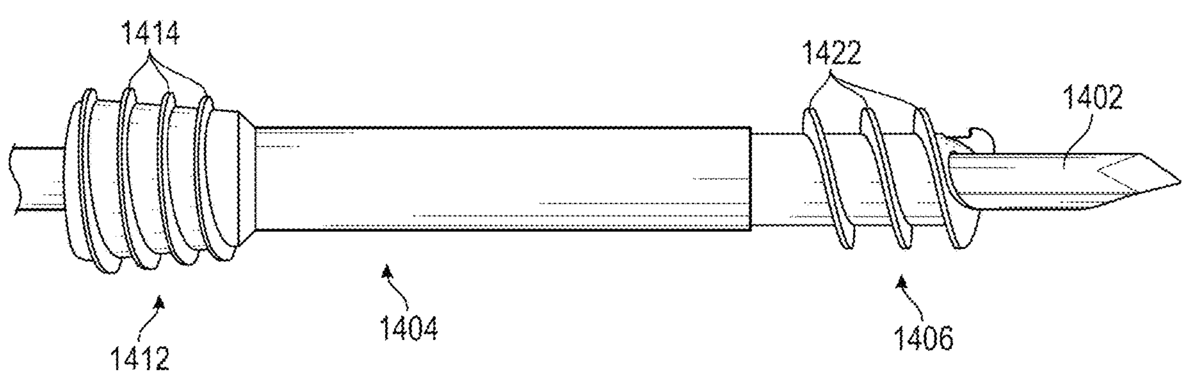

FIG. 18 is a side elevation view of a bone screw 1400 according to another embodiment of the present disclosure. Like the bone screw 1100 of FIGS. 11A through 15, the bone screw 1400 may be insertable into the bone over a guide wire 1402. The bone screw 1400 may also have a proximal member 1404, a distal member 1406, and a tension member (not shown) that is functionally similar to the tension member 1108 of FIGS. 11A through 15.

The proximal member 1404 may have a head 1412 with a generally conical shape, tapered such that the head 1412 has a diameter that decreases along the distal direction. The head 1412 may have proximal threads 1414. The proximal threads 1414 may also have a tapered major diameter and a tapered minor diameter, and may have a pitch that is smaller than the pitch of bone-engaging threads 1422 of the distal member 1406.

Thus, as the proximal threads 1414 engage the proximal bone portion and the bone-engaging threads 1422 of the distal member 1406, the proximal member 1404 may advance more slowly than the distal member 1406. This differential in rates of advancement may cause the bone screw 1400 to elongate, even as the head 1412 is being embedded in the proximal bone portion.

Such an embodiment may help distribute compressive stress from the head 1412 over a larger volume of bone, and may also avoid leaving any portion of the head 1412 protruding proximally from the proximal bone. More precisely, if desired, the head 1412 may be fully embedded in the proximal bone portion. If desired, the differential pitch between the proximal threads 1414 and the bone-engaging threads 1422 may be selected such that the bone screw 1400 reaches maximum length as the proximal surface of the head 1412 becomes flush with the exterior cortex of the proximal bone portion.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

As used herein, the term "proximal" means a location relatively closer to a user (i.e., a surgeon) when the user is installing the implant. The term "distal" means a location relatively further from the user. For example, when a user installs a bone screw into a material with a driver, the end of the bone screw engaged with the driver is the proximal end, and the tip of the bone screw that first engages the material is the distal end. The term "cannulated" means having a central bore extending along a longitudinal axis of a part between a proximal end and a distal end of the part.

Recitation of the term "first" with respect to a feature or element does not necessarily imply the existence of a second or additional such feature or element. Elements recited in means-plus-function format are intended to be construed in accordance with 35 U.S.C. § 112 (f). It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. As defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

The invention claimed is:

1. A bone screw insertable into a bone, the bone screw comprising:
- a proximal member;
- a distal member comprising bone-engaging threads, wherein the distal member is configured to slidably engage the proximal member such that a variable-length cavity is defined within the proximal member and the distal member; and
- a tension member residing at least partially within the variable-length cavity, the tension member comprising:
  - a proximal end coupled to the proximal member; and
  - a distal end coupled to the distal member such that, in response to motion of the distal member away from the proximal member, the tension member elongates and urges the distal member to move toward the proximal member;

wherein at least one of the proximal member and the distal member comprises a bending transmission feature, displaced either proximally or distally from a torque transmission feature that transmits torque from the proximal member to the distal member while permitting slidable engagement of the distal member relative to the proximal member, wherein the proximal member and the distal member are interconnected to share bending loads at the bending transmission feature.

2. The bone screw of claim 1, wherein the torque transmission feature has torque transmitting surfaces that are oriented closer to a radial direction than a to a circumferential direction, as to a cross section perpendicular to a longitudinal axis of the bone screw.

3. The bone screw of claim 1, wherein a proximal portion of the distal member, proximal to the bone-engaging threads, comprises an exterior diameter larger than a minor diameter of the bone-engaging threads.

4. The bone screw of claim 1, wherein:

the proximal member comprises a proximal member stop feature;

the distal member comprises a distal member distal stop feature configured to abut the proximal member stop feature to prevent further elongation of the tension member when the tension member is at a maximum length;

the tension member is at least partially formed of a superelastic material; and the maximum length is selected such that a superelastic strain level of the superelastic material is not exceeded.

5. The bone screw of claim 1, wherein the distal end comprises a distal member coupling interface that can be inserted through a second proximal end of the distal member and then coupled to the distal member from within the variable-length cavity.

6. The bone screw of claim 1, wherein the proximal member and the distal member cooperate to define a weakest cross section, as to bending stress, that is distal to a center of the bone screw.

7. The bone screw of claim 6, wherein the weakest cross section is positioned directly proximal to the bone-engaging threads.

8. The bone screw of claim 1, wherein:

the proximal member comprises a proximal interior surface that defines a proximal portion of the variable-length cavity;

the distal member comprises an extension extending proximally of the torque transmission feature, within the proximal portion; and the extension comprises the bending transmission feature, the bending transmission feature comprising an engagement surface that presses against the proximal interior surface in response to bending load applied between the proximal member and the distal member.

9. The bone screw of claim 8, wherein:

the proximal member comprises:

a proximal shank; and a head that is wider than the proximal shank; and the engagement surface is closer to the head than to the torque transmission feature.

10. The bone screw of claim 9, wherein:

the extension comprises:

a second distal end having the engagement surface; and a relief, distal to the engagement surface, having an outside diameter smaller than the engagement surface;

the proximal interior surface comprises a protrusion that protrudes toward a longitudinal axis of the bone screw and into the relief;

the protrusion acts as a proximal member motion stop feature; and the relief defines a shoulder that acts as a distal member motion stop feature configured to abut the proximal member motion stop feature to prevent further elongation of the tension member when the tension member is at a maximum length.

11. A bone screw insertable into a bone, the bone screw comprising:

a proximal member;

a distal member comprising bone-engaging threads, wherein the distal member is configured to slidably engage the proximal member such that a variable-length cavity is defined within the proximal member and the distal member; and a tension member residing at least partially within the variable-length cavity, the tension member comprising:

a first proximal end coupled to the proximal member; and a distal end coupled to the distal member such that, in response to motion of the distal member away from the proximal member, the tension member elongates and urges the distal member to move toward the proximal member;

wherein:

the distal end comprises a distal member coupling interface that can be inserted through an opening in a second proximal end of the distal member and then coupled to the distal member from within the variable-length cavity;

the opening is larger than the distal member coupling interface;

the distal member comprises a distal interior surface that defines a distal portion of the variable-length cavity;

the distal interior surface defines interior threading;

the distal member coupling interface comprises exterior threading engageable with the interior threading; and the first proximal end comprises a drive feature configured to facilitate rotation of the tension member to allow the exterior threading to engage with the interior threading.

12. The bone screw of claim 11, wherein:

the first proximal end of the tension member comprises an enlargement;

the proximal member comprises:

a proximal shank;

a head that is wider than the proximal shank;

a proximal interior surface that defines a proximal portion of the variable-length cavity; and a proximal aperture that provides access to the proximal portion of the variable-length cavity through the head;

the proximal aperture is sized to permit passage of the distal end of the tension member therethrough; and the proximal aperture defines a shoulder on which the enlargement rests upon coupling of the distal member coupling interface to the distal member.

13. The bone screw of claim 11, wherein:

the proximal member comprises:

a proximal shank;

a head that is wider than the proximal shank;

a proximal interior surface that defines a proximal portion of the variable-length cavity; and a proximal aperture that provides access to the proximal portion of the variable-length cavity through the head;

the distal member comprises:

a distal aperture that provides access to the distal portion of the variable-length cavity; and the proximal aperture and the distal aperture are sized to permit passage of a K-wire therethrough.

* * * * *